(12) United States Patent
Ivarsson

(10) Patent No.: US 6,714,303 B2
(45) Date of Patent: *Mar. 30, 2004

(54) ANALYTICAL METHOD AND APPARATUS

(75) Inventor: Bengt Ivarsson, Bälinge (SE)

(73) Assignee: Biacore AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/244,819

(22) Filed: Sep. 16, 2002

(65) Prior Publication Data

US 2003/0067612 A1 Apr. 10, 2003

Related U.S. Application Data

(63) Continuation of application No. 09/368,461, filed on Aug. 4, 1999, now Pat. No. 6,493,098.

(30) Foreign Application Priority Data

Feb. 4, 1997 (SE) ............................................. 9700384
Feb. 3, 1998 (WO) ................................ PCT/SE98/00196

(51) Int. Cl.$^7$ ........................ G01N 21/55; G01B 11/28
(52) U.S. Cl. ...................................... 356/445; 356/630
(58) Field of Search ........................ 356/445, 446–448, 356/630–632

(56) References Cited

U.S. PATENT DOCUMENTS 6,493,097 B1 * 12/2002 Ivarsson ..................... 356/630

FOREIGN PATENT DOCUMENTS

| EP | 286 195 A2 | 10/1988 |
|----|------------|---------|
| WO | WO 90/05295 | 5/1990 |
| WO | WO 93/14392 | 7/1993 |

OTHER PUBLICATIONS

Berger et al., "Resolution in surface plasmon microscopy," *Review of Scientific Instruments* 65(9): 2829–2836, 1994.
Hayashi et al., "Experimental instrument for observing angle– and frequency–scanned attenuated total reflection spectra," *Review of Scientific Instruments* 67(9): 3039–3043, 1996.
Karlsen et al., Simultaneous determination of refractive index and absorbance spectra of chemical samples using surface plasmon resonance, *Sensors and Actuators B*(Part II): 747–749, 1995.
Knoll, "Optical Characterization of Organic Thin Films and Interfaces with Evanescent Waves," *MRS Bulletin* 16: 23–39, 1991.
Lenferink et al., "An improved optical method for surface plasmon resonance experiments," *Sensors and Actuators B3*(4): 261–265, 1991.

* cited by examiner

Primary Examiner—Frank G. Font
Assistant Examiner—Amanda Merlino
(74) Attorney, Agent, or Firm—Seed IP Law Group PLLC

(57) ABSTRACT

A method of examining thin layer structures on a surface for differences in respect of optical thickness, which method comprises the steps of: irradiating the surface with light so that the light is internally or externally reflected at the surface; imaging the reflected light on a first two-dimensional detector; sequentially or continuously scanning the incident angle and/or wavelength of the light over an angular and/or wavelength range; measuring the intensities of light reflected from different parts of the surface and impinging on different parts of the detector, at at least a number of incident angles and/or wavelengths, the intensity of light reflected from each part of the surface for each angle and/or wavelength depending on the optical thickness of the thin layer structure thereon; and determining from the detected light intensities at the different light incident angles and/or wavelengths an optical thickness image of the thin layer structures on the surface. According to the invention, part of the light reflected at said surface is detected on a second detector to determine the incident angle or wavelength of the polarized light irradiating the surface. An apparatus for carrying out the method is also disclosed.

24 Claims, 20 Drawing Sheets

65.9°

66.4°

ANALYTICAL METHOD AND APPARATUS

CROSS-REFERENCE TO RELATED APPLICATION

This application is a continuation of U.S. patent application Ser. No. 09/368,461 filed Aug. 4, 1999 now U.S. Pat. No. 6,493,098 and allowed Jun. 18, 2002, which claims priority from co-pending PCT Application No. SE98/00196, filed Feb. 3, 1998, which claims priority from Swedish Application No. 97003842, filed Feb. 4, 1997, all of which applications are incorporated herein by reference in their entirety.

BACKGROUND OF THE INVENTION

1. Field of the Invention

The present invention relates to a method and an apparatus for optical surface analysis of a sample area on a sensor surface.

2. Description of the Related Art

The interest for surface sensitive measuring techniques has increased markedly recently as several optical techniques have been developed for identifying and quantifying molecular interactions, which techniques do not require labelling. The most used optical technique so far is based on surface plasmon resonance, hereinafter frequently referred to as SPR.

The phenomenon of surface plasmon resonance, or SPR, is well known. In brief, SPR is observed as a dip in intensity of light for a specific wavelength reflected at a specific angle (as measured by, e.g., a photodetector) from the interface between an optically transparent material, e.g., glass, and a thin metal film, usually silver or gold, and depends on among other factors the refractive index of the medium (e.g., a sample solution) close to the metal surface. A change of the real part of the complex refractive index at the metal surface, such as by the adsorption or binding of material thereto, will cause a corresponding shift in the angle at which SPR occurs, the so-called SPR-angle. For a specific angle of incidence, the SPR is observed as a dip in intensity of light at a specific wavelength, a change in the real part of the refractive index causing a corresponding shift in the wavelength at which SPR occurs.

To couple the light to the interface such that SPR arises, three alternative arrangements may be used, viz., either a metallized diffraction grating (see H. Raether in "Surface Polaritons", Eds. Agranovich and Mills, North Holland Publ. Comp., Amsterdam, 1982), a metallized glass prism (Kretschmann configuration) or a prism in close contact with a metallized surface on a glass substrate (Otto configuration). In a SPR-based assay, for example, a ligand is bound to the metal surface, and the interaction of this sensing surface with an analyte in a solution in contact with the surface is monitored.

Originally, collimated light was used for measuring the SPR-angle, the sensing area being restricted to the intersection of the collimated light beam and the metal surface. The apparatus used was based on mechanical goniometry with two movable mechanical axes carrying the illumination and detecting components, the rotational center of which was placed in the center of the sensor area, i.e., one axis for the incident light and another axis for the reflected light which was detected by a single photodetector. A plane-sided coupling prism at total internal reflection condition was used to preserve the collimated beam inside the prism, which, however, introduced a refraction at non-orthogonal incidence at the prism, thereby introducing a beam-walk at the metal surface. A half-cylindrical coupling lens with orthogonal incidence of the optical axis of the light gave a fixed sensor area, however, introduced a beam-convergency, i.e., a non-collimated or quasi-collimated beam inside the prism.

In a development, the movable opto-mechanical axis on the illumination side was eliminated by using a focused incident beam, so-called focused attenuated total reflection (focused ATR), as described by Kretschmann, Optics Comm. 26 (1978) 41–44, the whole angular range simultaneously illuminating a focal line or point of a given sensing surface. The use of a detector matrix for detecting the reflected light eliminated the movable opto-mechanical axis also on the reflectance side, providing a faster SPR-detection than that of the prior art. Such systems are described in, e.g., EP-A-305 109 and WO 90/05295. In the latter, light beams reflected from a specific sub-zone at the sensor area are imaged anamorphically so that beams in one plane (the sagittal plane) create a real image on a specific detector-pixel row of a matrix detector, permitting the occurrence of a local surface binding reaction to be identified, while quantification of the reaction is obtained via angular data for a reflectance curve measured along the same pixel row, where the reflectance curve is created by beams in a plane (the meridian plane) normal to the first-mentioned plane. Thus, one dimension of the matrix detector is used for real imaging simultaneously as the other dimension is used for only angular measurement. This permits only sub-zones arranged in a row to be simultaneously monitored and imaged.

In a variation of goniometry, the bulky mechanical axes were replaced by rotating or vibrating mirrors, respectively. A disadvantage of that approach is, however, that when scanning the incident angle by means of a plane mirror, the point where the light beam hits the sensor surface will move along the internal reflection surface of the prism. This problem was avoided by using a combination of rotating mirror and focused SPR, e.g., as described by Oda, K., Optics Comm. 59 (1986) 361. In this construction, a first collimated beam of about 1 mm diameter impinges on the rotational center of a rotating mirror placed at the focal length of a focusing lens, thus producing a second quasi-collimated beam, the distance of which to the optical axis depends on the reflecting angle of the mirror. The second collimated beam is focused by a second focusing lens onto a prism base at total internal reflection conditions. During the rotation of the mirror, the angle of incidence at the approximately fixed sensor area is scanned for the quasi-collimated beam.

Another approach to obtain a fixed and also enlarged sample spot is proposed by Lenferink et al., "An improved optical method for surface plasmon resonance experiments", vol. B3 (1991) 261–265. This technique uses the combination of a collimated light beam illuminating a plane rotating mirror, a focusing cylindrical (convex) lens after the mirror and a half-cylinder lens for coupling the light to the sensing surface. By making the cylindrical lens focus the light on the focal surface of the coupling half-cylinder, using a relatively complex lens system, a collimated beam is obtained inside the coupling prism.

Other optical techniques similar to SPR are Brewster angle reflectometry (BAR) and critical angle reflectometry (CAR).

When light is incident at the boundary between two different transparent dielectric media, from the higher to the lower refractive index medium, the internal reflectance varies with angle of incidence for both the s- and p-polarized components. The reflected s-polarized component increases with the angle of incidence, and the p-polarized component shows a minimum reflectance at a specific angle, the Brewster angle. The angle at which both s- and p-polarized light is totally internally reflected is defined as the critical angle. For all angles of incidence greater than the critical angle, total internal reflection (TIR) occurs.

Schaaf et al., Langmuir, vol. 3 (1987) describes Brewster angle reflectometry using a micro-controlled rotation table and a movable detector in scanning angle reflectometry around the internal Brewster angle to study a protein (fibrinogen) at a silica/solution interface. The use of movable optomechanical axes and a rotation table gives a slow measuring procedure, and the sensor area is restricted to the cross-section of the collimated light beam with the sensor surface being limited by the need for non-beam-walking.

A focusing critical angle refractometer, based on a wedge of incident light which strikes the line of measurement, including the critical angular interval to be measured, and which measures the one-dimensional refractive index profile along a focused line immediately adjacent to the glass wall of a liquid container is described by Beach, K. W., et al., "A one-dimensional focusing critical angle refractometer for mass transfer studies" Rev. Sci. Instrum., vol. 43, 1972. This technique is limited in that it enables only a one-dimensional sensor area, which is restricted to the cross-section of the light line with the sensor area.

In all the above described prior art methods for reflectometric measurements, the reflectometric signal obtained represents an average value for the sensor surface and the size of the sensor surface is restricted, or minimized, to the extension of the collimated or quasi-collimated narrow beam, or focusing point or line. Therefore, such SPR-based methods used to measure, for example, inter alia protein interactions are limited to quantitative information for sensing areas localized in one spot or one row of spots on the surface where a specific interaction takes place. Approaches to monitor a two-dimensional interaction pattern have been made for both macroscopic and microscopic SPR-based imaging of a sensing surface.

Thus, EP-A-341 928 discloses a method for monitoring a large SPR sensor area in real-time by scanning a small focused beam, of, e.g., 10 µm, as a measuring sensing surface successively over the large area, more specifically a DNA sequencing gel, for example 20×20 $cm^2$, thereby making it possible to build up an image or picture of the sample distribution within the sequencing gel by means of a photodetector array. This method requires, however, the use of scanning mirrors for both addressing the sensor zones and scanning the angle and complex and expensive processing of angular and positional data from the mirror-scanners and photodetectors, which limits the detection rate.

Yeatman and Ash, Electronic Letters 23 (1987) 1091–1092, and SPIE 897 (1988) 100–107 disclose microscopic real imaging of the sensing surface, so called surface plasmon microscopy, or SPM. This was achieved by the use of SPR in the Kretschmann configuration with a triangular prism for imaging dielectric patterns deposited on a silver film with a lateral resolution of about 25 µm, utilizing a focused beam in the form of a line scanned along the sensor surface. Also described is the use of an expanded laser beam at the resonance angle to illuminate a larger area and make a photograph of such an image by a positive lens in front of the photodetector. The illuminating beam is collimated and the angle of incidence is adjusted by rotating the triangular prism. The method is proposed to be used for the examination of metal films, biological and other superimposed monolayers.

Image processing methods for such SPM using a collimated beam and a lens inserted into the reflected beam to create an image of the sample distribution at the prism base are discussed in by Yeatman and Ash in "Computerized Surface Plasmon Microscopy", SPIE, Vol. 1028 (1988) 231.

Okamoto and Yamaguchi have described a SPR-microscope wherein the position of a collimated beam, SPIE vol. 1319 (1990) 472–473, or a focused beam, Optics Communications 93 (1992) 265–270, is scanned across the sample surface in a Kretschmann configuration, the assembled point-SPR data thereby creating an image. In the focused beam alternative, a linear photodiode array is used for detection of the SPR-angle, in accordance with the principle of focused ATR as described earlier by Kretschmann, supra.

Drawbacks with mechanically scanned SPR-sampling includes that a high lateral resolution and high speed for "real time monitoring" demands a complex and expensive scanning mechanics (due to the bulkiness of the illumination and detection device).

EP-A-469377 describes an analytical system and method for the determination of an analyte in a liquid sample based on surface plasmon imaging. Surface plasmon images as a function of the angle of incidence are monitored by a CCD-camera and analyzed by an image-software. Algorithms are used for comparing the measured SPR-angle for different areas of the sensor surface for the purpose of eliminating the contribution from a non-specific binding, and of calibration the response curve.

Rothenhausler and Knoll, Nature, 332 (1988) 615–617, demonstrates surface plasmon microscopy on organic films (a multilayer cadmium arachidate), based on SPR in a Kretschmann configuration. A simple lens is used to form an image of the sample/metal interface. A collimated beam (plane waves) illumination and a movable bulky optomechanical axis are used to change the angle of incidence.

In the above prior art arrangements for SPM, the angle of incidence is varied by the use of goniometry, either in a form where one or both optomechanical axes are moved (scanned) in relation to a fixed prism, or in a form using a movable optomechanical axis in combination with a rotating prism, the common rotation point being in the center of the prism sensor surface, and the angle of incidence being derived from the change in position or rotation of the mechanical axis through mechanical, electronic, electromagnetic or optical means. It is readily understood that such variation of the incident angle based on rotation of the mechanical axis carrying illuminating, imaging and detector modules is rather slow and inaccurate if not a complex and expensive design is provided.

Another approach is disclosed by Kooyman and Krull, Langmuir 7 (1991) 1506–1509, namely SPM using a small vibrating mirror in combination with a Kretschmann configuration to adjust the angle of incidence. A disadvantage is, however, that the probed spot is not stationary during the angular scan, i.e., all sites within a sensing area are not probed by light at an equal angle of incidence range, unless bulky optics is covering the sensing area at an excess.

Also microscopy based on Brewster angle measurements has been described. Hènon and Meunier, Rev. Sci. Instrum., vol. 62 (1978) 936–939 discloses the use of a microscope at the Brewster angle for direct observation of first-order phase transitions in monolayers. In this case, external Brewster angle is measured, i.e., no internal reflection and no coupling prism, the camera plane being parallel with the sensor surface.

Similarly, Hönig and Mobius, J. Phys. Chem., vol. 95 (1991) 4590–4592 describes the use of Brewster angle microscopy to study the air-water interface. Objects of about 3 μm diameter could be visualized by video recording of p-polarized light reflected under a fixed Brewster angle for the pure water surface.

A microscopic imaging ellipsometer has been described by Beaglehole, D., Rev. Sci. Instrum., 59 (12) (1988) 2557–2559.

Multiple-angle evanescent wave ellipsometry, in the form of using rotating optical means and a rotating prism for the variation of incident angle, and a phase-modulated ellipsometer, has been used for studying the polymer (polystyrene) concentration profile near a prism/liquid interface; see Kim, M. W., Macromolecules, 22, (1989) 2682–2685. Furthermore, total internal reflection ellipsometry in the form of stationary optical means at a single angle of incidence has been suggested for quantification of immunological reactions; see EP-Al-O 0 67 921 (1981), and EP-Al-0 278 577 (1988).

Azzam, R. M. A., Surface Science 56 (1976) 126–133, describes a use of evanescent wave ellipsometry, wherein both the intensity and polarization ellipse of the reflected beam can be monitored as functions of the angle of incidence, wavelength or time. Under steady state conditions, measurements as a function of wavelength and angle of incidence can provide basic information on the molecular composition and organization of the (biological) cell periphery. In a dynamic time-varying situation, measurements as a function of time can resolve the kinetics of certain surface changes.

Abelès, F. et al., in Polaritons, Editor E. Burstein and F. De Martini, Pergamon Press, Inc., New York, 1974, 241–246, shows how extremely sensitive surface plasmons are to very fine modifications of the surface, and the advantage of then measuring not only the reflected amplitude, but also the ellipsometric parameters, amplitude and phase, of the reflected wave.

A focusing critical angle refractometer for measuring a one-dimensional refractive index profile being displayed in a graphic image for mass transfer studies has been described by Beach, K. W., The Review of Scientific Instruments, 43, No. 6 (1972) 925–928. Since this apparatus uses one dimension in the image plane for a real image, and the other dimension for projecting the reflectance versus angle of incidence, it could not, however, provide a two-dimensional image of the refractive index distribution.

The prior art microscopy systems described above do not permit a sufficiently rapid, sensitive and accurate scanning and measurement of the incident angle to permit highly quantitative multi-site real-time monitoring of a sensor surface. Further, they are only suitable for imaging a limited sensor area of up to about 1×1 mm². They are also too laborative and operator-dependent to be used in a commercial analytical instrument.

More particularly, the prior art apparatuses and systems for SPR microscopy and Brewster angle microscopy use either a high inertia scanner in the form of a goniometer where one or both mechanical axes for the illumination side and the imaging side, respectively, are rotated in relation to a fixed prism, or a movable mechanical axis in combination with a rotating prism for scanning the optical axis, i.e., the angle of incidence. In case the illumination consists of a collimated beam of light, the incident angle is measured directly on the angle steering signal without using the incident light, e.g., on the control signal to the rotor-driving motor of a mirror, or by an electronic or optoelectronic angle sensor placed on or at the rotated axis. Alternatively, a galvanometric or resonant low inertia scanner is used to drive a vibrating mirror to oscillate within a given calibrated angular range, determined by a given drive current, without monitoring the actual incident angle of the light.

The necessary high refractometric sensitivity for determining the refractive index of the sensor surface with an apparatus constructed according to the above prior art in a long-term accurate commercial analytical instrument could therefore only be achieved with a very complex and expensive design.

BRIEF SUMMARY OF THE INVENTION

It is an object of the present invention to overcome the above disadvantages and provide an optical method and apparatus that permits microscopic as well as large area analysis of the sensing surface of a sensor chip or plate with a high refractometric sensitivity and accuracy at high spatial resolution.

According to the present invention, the above object is obtained in a large area or microscopy analytical apparatus of the above described types, as well as in others, by using part of the angular or wavelength-scanned light that illuminates the sensor chip for monitoring and determining the momentary incident angle or wavelength of the light.

As will be further explained below, this enables an improved quantitative measuring precision, accuracy and speed in the determination of the angle of incidence (alternatively wavelength) corresponding to the local reflection curve parameters, e.g., reflectance minimum, at the surface structures on the sensor surface, such as surface-distributed reaction sites.

In one aspect, the present invention provides a method of examining thin layer structures on a surface for differences in respect of optical thickness, which method comprises:
  irradiating the surface with light so that the light is internally or externally reflected at the surface,
  imaging the reflected light on a two-dimensional first photodetector,
  sequentially or continuously scanning the incident angle and/or wavelength of the light over an angular and/or wavelength range,
  measuring the intensities of light reflected from different parts of the surface and impinging on different parts of the detector, at at least a number of incident angles and/or wavelengths, the intensity of light reflected from each part of the surface for each angle and/or wavelength depending on the optical thickness of the thin layer structure thereon,
  and determining from the detected light intensities at each of the different light incident angles and/or wavelengths an optical thickness image of the thin layer structures on the surface,
  which method is characterized in that part of the light reflected at the surface is detected on a second photodetector to monitor the incident angle or wavelength of the polarized light irradiating the surface.

In another aspect, the present invention provides an apparatus for examining thin layer structures on a surface for differences in respect of optical thickness, comprising:
  a sensor unit having a sensing surface with a number of zones capable of exhibiting thin layer structures of varying optical thickness, particularly as the result of contact with a sample, a light source for emitting a beam of light, optical means for coupling said light beam to said sensor unit, first photodetector means, means for sequentially or continuously scanning said light incident at said sensor surface over a range of incident angles and/or wavelengths, means for imaging light reflected from said different parts of the sensor surface onto said first photodetector means for detecting the intensities of the reflected light, means for determining each said angle and/or wavelength of light impinging on said sensing surface, evaluation means for determining from the relationship between detected intensity of the reflected light and incident light angle and/or wavelength, the optical thickness of each zone of said sensor surface to thereby produce and monitor a morphometric image of the optical thickness of the sensor surface, which apparatus is characterized in that it comprises second photodetector means, and that said means for determining said light angles and/or wavelengths comprise means for focusing a part of said light reflected at the sensing surface onto said second photodetector means, wherein each position of said focused light on said second photodetector means is related to a specific angle and/or wavelength of the light incident at the sensing surface.

The term "optical thickness" as used herein defines a composite optical property of a material that is a function of both its physical thickness and its refractive index.

The term "surface structures" as used herein means any chemical, physical, biophysical and/or biochemical structures of thin or other type on a sensor surface, especially structures produced via chemical or biochemical interactions with species immobilized on the sensor surface.

It is understood that in accordance with the present invention, a series of images of a sensor surface are created, one image for each specific incident angle or wavelength. A part of the imaging detector, or a separate detector, is used for measuring the incident angle or wavelength. This will be described in more detail further below.

The light is usually polarized prior to hitting the photodetector. This may be accomplished by using a light source which emits polarized light or by placing a polarizer between the light source and the detector.

In one basic embodiment of the invention, monochromatic angularly scanned light is used, and a main first part of the reflected collimated beam is used to produce a real image on a first main area of the matrix photodetector, while a second part of the reflected collimated beam is focused into a sharp line on a second specific minor linear area of the matrix photodetector. During the angular scan of the collimated beam the change in angle of incidence is determined through the change in position of either the maximum, or the centroid of the focused light intensity detected by the detector elements along the linear detector area by use of an intensity-curve analysis algorithm.

In another basic embodiment of the invention, a scanned monochromatic light at a fixed angle of incidence is used, and the second part of the reflected fixed collimated beam passes a wavelength dispersive element, and is then focused into a sharp point or line on a second specific minor linear area of said matrix detector. During the wavelength scan of the beam the change in wavelength is determined through the change in position of either the maximum, or the centroid of the focused light intensity detected by the detector elements along the linear detector area by use of an intensity-curve analysis algorithm.

In a preferred embodiment, the present invention provides an improved reflectometric performance for an imaging method based on total internal reflection, such as e.g., surface plasmon resonance (SPR), or external reflection, such as external Brewster angle spectroscopy or ellipsometry, by the use of a novel optical design which will be further described below and comprises a bifocal imaging system enabling simultaneous sensor zone resolution and projection of rays for measurement of the angle of incidence, and of the wavelength, on the same matrix photodetector array, and a low inertia mirror scanner system for a mainly stationary illuminated area of the sensor chip in combination with a total internal reflection element, or a grating, for coupling an evanescent wave to the sensor surface.

More particularly, such an apparatus may comprise an imaging system having two different focal lengths in the same plane of projection (meridian plane), together with an identical focal length for the sagittal plane and the dominating part of the meridian plane, and a common photodetector matrix array for image and angle monitoring. Preferably, the main part of the detector array lies in the real image plane of the imaging system, while a minor part of the detector matrix array lies in the back focal plane of the imaging system. Detector elements within the real image plane monitor light intensity originating from specific local spots at microscopic lateral resolution, while other detector elements within the back focal plane detect the position of the focused line, i.e., the angle of incidence.

In an alternative form, the bifocal imaging enables detector elements within the real image plane to monitor light intensity originating from a specific local spot at microscopic lateral resolution, while other detector elements within the back focal plane detect the position of the focused line corresponding to the wavelength.

The reflected light intensity varies with the angle of incidence, mainly due to the angle dependent reflection coefficient, but may also vary due to a movement of the illuminated area if the light intensity across the illuminating beam is not constant. By use of an approximately stationary illuminated sensor area, together with an image-intensity normalization algorithm, a highly resolved light intensity of the local reflectance curves may be detected, which enables a high resolution in the determined angle/wavelength at the corresponding reflectance minima or maxima or centroid.

While it is preferred that the same detector array component is used for both image detection and angle or wavelength detection, separate detectors may, of course, also be used.

When both incident angle and wavelength of the light are to be measured, the detector may be divided into two (smaller) parts, and a larger part, wherein one of the smaller parts is used for detection of the incident angle, and the other smaller part is used for detection of the wavelength, and the larger detector part is used for imaging.

As stated above, the present invention is characterized by an integral detection of both image and incident light angle and/or wavelength to obtain a better accuracy and sensitivity in the multi-zone reflectometry and a faster analysis procedure than those obtained in the prior art. Thus, according to the present invention, the same collimated light is used (i) to illuminate each point on the sensor surface with a practically identical angle of the incident light, permitting a minimum deviation (a maximum deviation of 0.002°) within the whole sensor area for a large angular/refractometric dynamic range, and (ii) to measure changes in this angle for each zone with a resolution of the order of 0.0001°.

Thus, by integrating into the structure (i) a detector for a highly resolved image of, for example, a multi-zone sensor surface, and (ii) a detector for the angle and/or wavelength, respectively of the incident light, and thereby reduce the sources of error for the measurement of angle and wavelength, respectively, and their relation to a specific sensor subzone representation on the photodetector matrix, the following advantages may be obtained in relation to the prior art apparatus constructions:

- A higher resolution of absolute and relative reflectance minimum angle,
- a higher resolution of absolute and relative reflectance minimum wavelength,
- a higher image contrast and resolution of image contrast,
- a higher frequency for reflectance image data detection,
- a higher optomechanical robustness (less wear, lower maintenance cost),
- a smaller total volume for the optomechanical apparatus, which permits an improved (cheaper, quicker) thermostatting, and thereby improved measuring system performance.

The apparatus according to the invention may use any of a number of optical principles for the scanning of the angle of incidence of the collimated beam, known to those skilled in art, including the principles described above in the description of the prior art, as long as the beam deflecting principle selected provides an angularly scanned collimated beam incident on a sensor surface at total internal reflection conditions, in either a Kretschmann or Otto prism configuration, or a grating coupling configuration, during the probing of a mainly stationary area.

Exemplary such scanning principles are reflective beam steering through mirrors or reflection diffraction gratings, and transmissive beam steering through refracting scanners, or through transmission diffraction gratings or transient gratings (acousto-optical scanning). These beam-steering principles may be combined into suitable scanner configurations known to a person skilled in the art.

Likewise, the optical system principle for the determination of reflection versus angle and/or wavelength of incidence may be selected from a number of optical principles known to a person skilled in art, including those described above in the description of the prior art. Exemplary such optical principles are surface plasmon resonance (SPR), Brewster angle (both internal and external), ellipsometry angle (both internal and external), critical angle, and frustrated total reflection waveguide resonance.

In the case of also an evanescent wave absorbing sample interaction with the sensing zone, the change in the complex refractive index corresponds not only to a shift in the SPR-angle or SPR-wavelength (related to the changed real part of the complex refractive index) but also to a shift in depth of the intensity at the resonance.

For sensor applications involving absorbance, the apparatus according to the invention may operate for reflectance-absorption imaging.

In the case of the incident light being coherent, a spatially heterogeneous sensing surface in terms of optical thickness or refractive index modulates the relative phase of the evanescent wave, creating a stationary interference pattern in the image or real image obtained. The incident light may after the total internal reflection interfere with light partially reflected at another interface of the sensor unit, e.g., on the opposite side to the sensor surface substrate interface on the substrate. When, for example, a sample molecule is specifically bound to certain areas within this sensing surface, the interference fringes move into new positions. By tracking the position of specific fringes by use of image process software, in relation to the scanned angle or wavelength of incidence, the local surface concentration changes may be interferometrically monitored by the apparatus according to the invention. The interferometric feature of phase-sensitive evanescent wave detection may increase the refractometric sensitivity in, for example, interferometric surface plasmon resonance image analysis, or interferometric Brewster angle and critical angle image analysis.

Generally, the present invention creates an optically densitometrically (refractometrically) quantitated image of a sensing surface pattern in approximative real-time by momentarily detecting the polarized light reflectance of the sensing surface. While the reflectance in the sensing surface preferably is internal, i.e., the light enters from a dielectric medium of a higher refractive index towards a dielectric medium of a lower refractive index, the reflectance may also be external, i.e., the probing light passes through a layer, such as a sample layer, to be probed on the sensor surface, e.g., external Brewster angle reflectometry and external ellipsometry.

Hereinafter, the present invention will be described in more detail, by way of example only, with regard to some embodiments of the invention. Reference is made to the accompanying drawings, wherein identical parts throughout the Figures are indicated by the same reference designations.

DETAILED DESCRIPTION OF THE INVENTION

As mentioned above, the present invention relates to an optical method and apparatus for large area or microscopical analysis of structures on a sensor surface, such as real-time monitoring of a chemical sensor or biosensor surface. Usually, the sensor surface has a plurality of individual subzones or areas at which different interactions may take place and produce thin layer structures of optical thicknesses that differ between the subzones. Such "multi-spot" surfaces may be used for a variety of analytical purposes. For example, a surface supporting different ligands on the surface may be subjected to a sample that may contain one or more species, or analytes, capable of binding to respective ligands on the surface. Thereby a sample may be analyzed for the presence of several analytes "in one shot". Other examples and uses are readily apparent to the skilled person.

According to the invention, the sensor surface in question is subjected to illumination with, usually, collimated light on a mainly constant illuminated area and area position, and both image and angle of incidence, and in an alternative form where more than one wavelength is sequentially incident, also wavelength, are simultaneously monitored by use of the same or another multichannel photodetector or matrix photodetector array than that used for the imaging. A characteristic feature of the invention is that a (usually minor) part of the angular or wavelength-scanned light that illuminates the sensor area for imaging purposes is used to determine the momentary incident angle or wavelength of the light. In that way, the momentary incident light angle or wavelength may be directly correlated with the simultaneously produced momentary image of the sensor surface, permitting convenient quantification of the surface subzones where, e.g., a surface binding interaction has taken or takes place.

Figure 1:
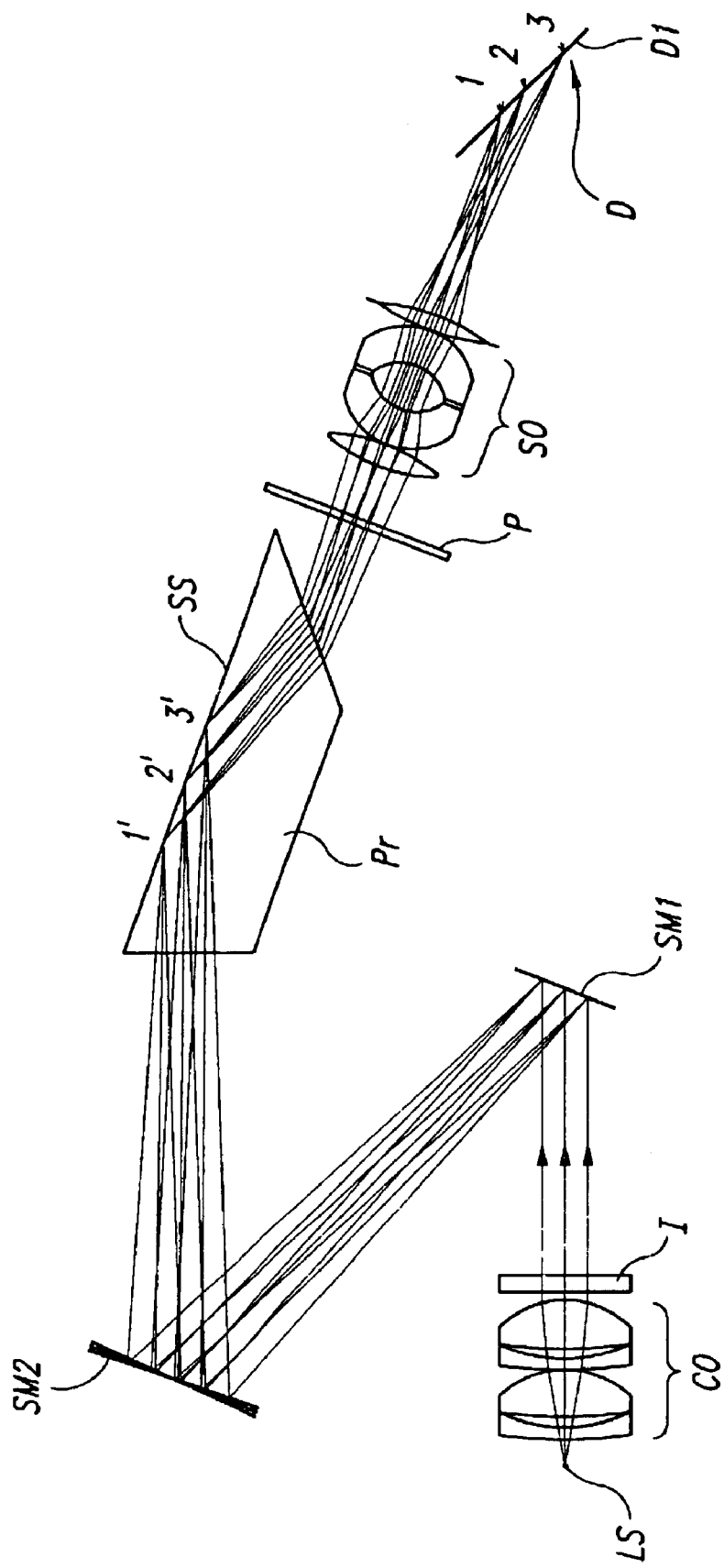
FIG. 1 is a schematic meridian view of an embodiment of an optical sensor apparatus and light ray paths thereof according to the present invention, which embodiment is based on scanning of the angle of the incident light.

FIG. 1 schematically shows a total internal reflection-based embodiment of optical system and ray path according to the present invention, which for the purpose of illustration only is assumed to be a biosensor, for example, of the type described in U.S. Pat. No. 5,313,264 and in Jonsson, U., et al., BioTechniques 11:620–627 (1991).

In the system of FIG. 1, a light source, LS, illuminates a collimator optics, CO, to produce a parallel light beam which passes an interference filter, I, as a monochromatic beam and impinges on a first flat scanner mirror, SM1 to be deflected onto a second scanning mirror, SM2. The latter deflects the beam into a means for coupling the light to a sensor surface, SS. In the illustrated case, this coupling means is a prism, Pr, but may also be a grating as is well known in the art.

The sensor surface may be any of a variety of sensor surfaces (which are known or will be known in the future) and, while its basic material structure largely depends on the optical detection principle used, it usually comprises an outer reactive layer, for example having different specific reactive ligands, e.g., antibodies, antigens, nucleic acid fragments, cells or cell fragments, etc., immobilized on defined subzones. An exemplary biosensor element for SPR is described in EP-A-442922, whereas exemplary reactive biosensor surfaces are described in U.S. Pat. No. 5,242,828 and U.S. Pat. No. 5,436,161. The latter comprise a hydrogel (for SPR purposes bound to a gold or silver film), such as dextran, which supports or is capable of covalently binding ligands for reaction with sample analytes.

The sensor surface may further be based on biophysical reactions, where the specific sample interaction results in a structural change manifested as a change in the thickness/refractive index distribution, including absorption, of the sensor layer. Such biophysical interactions include, for example, protein crystallization, formation of protein aggregates caused by precipitation, agglutination or flocculation reactions; the adhesion of membrane complexes, such as biological cells and cell membrane fragments. For further details on the detection of biophysical interactions on a sensor surface it is referred to our copending international application PCT/SE96/01074.

While the sensor surface may be constructed directly on prism Pr in FIG. 1, the system described in U.S. Pat. No. 5,313,264, referred to above, uses an elastic optical interface ("optointerface") for coupling the light between the prism and the sensor surface. Exemplary optical interface designs are described in U.S. Pat. No. 5,164,589 and our copending international application No. PCT/SE96/01522.

The sensor surface is (in the illustrated case) assumed to be exposed on its upper side to a sample containing analytes. The sample may advantageously be contacted with the sensor surface in a flow type cell, e.g., as described in the aforementioned U.S. Pat. No. 5,313,264 where one or more flow cells are defined by the sensor surface being docked against one or more open channels in a fluidic block or cartridge.

With reference again to the ray path in FIG. 1, the beam is totally internally reflected at the sensor interface side of the coupling prism. The p-polarized component of the beam then passes a polarizer, P, and a main first part of the beam is directed into a first main part of an objective, which main part consists of a spherical objective, SO, producing a real image on matrix detector array, D, of the light intensity reflected from the sensor surface area. The detector array D is arranged such that the real image of the sensor area is produced on a first rectangular main part, D1, of the array. That is, the first part, SO, of the objective has its real image plane positioned at the plane of the photodetector array. Reference signs 1, 2 and 3 at the detector array D denote the respective images of the corresponding subzones on the sensor surface SS, indicated at 1', 2' and 3', respectively.

The two scanning mirrors, SM1 and SM2, have a related rotational movement which produces an angularly scanned collimated beam incident within a range of angles of incidence on the sensor surface side of the prism Pr. As is readily appreciated by the skilled person, the "beam walk" of the illuminated area may be reduced by a suitable choice of the distances between mirrors and prism, and scanned angular range of the mirrors.

Figure 2:
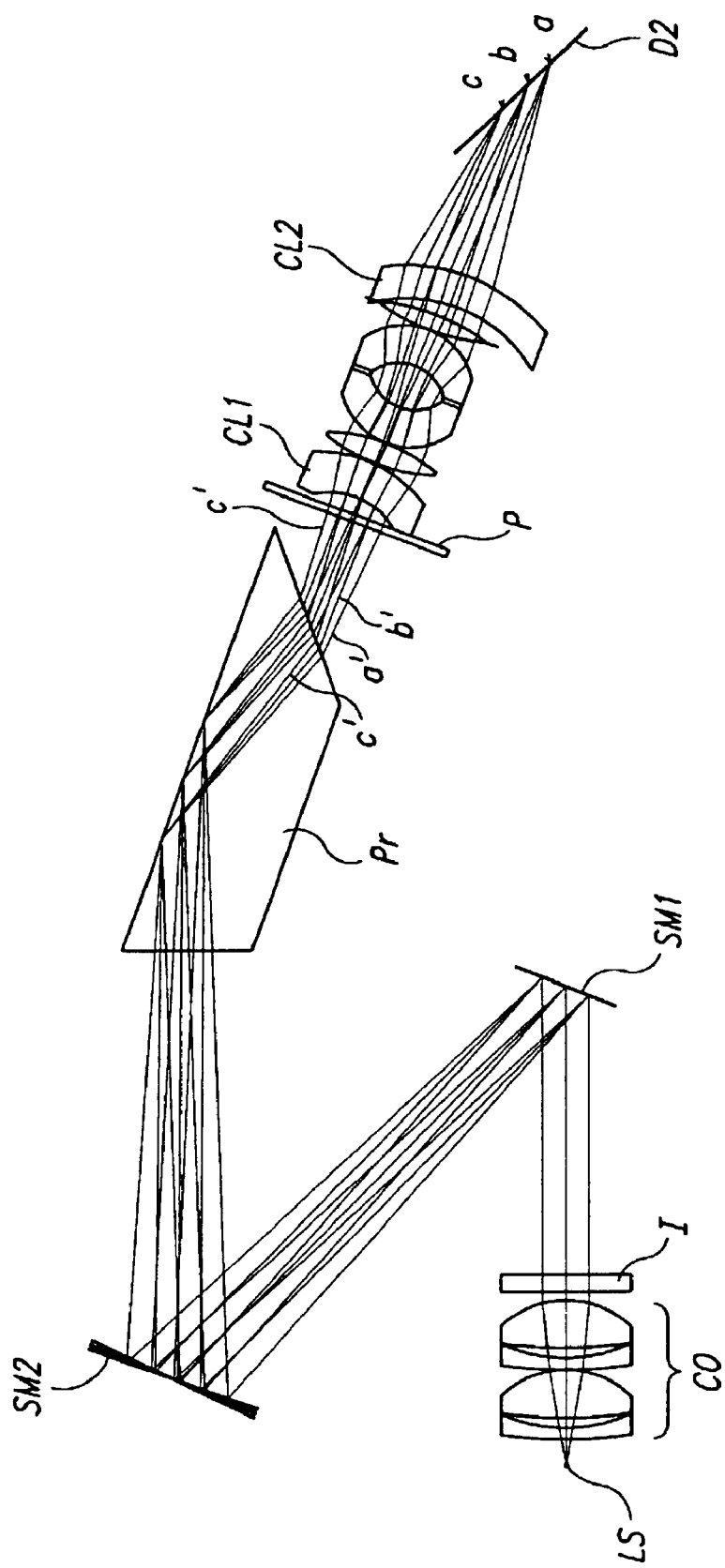
FIG. 2 is another, parallel schematic meridian view of the embodiment shown in FIG. 1.

Whereas only the above-mentioned first part of the objective is shown in FIG. 1, the remaining or second part of it is shown in FIG. 2, which is a meridian view of the optical biosensor system parallel to that in FIG. 1 and illustrates how the ray path for a second minor part of the beam is directed into the second, minor part of the objective consisting of the spherical objective SO, mentioned above, combined with two cylindrical lenses, CL1 and CL2. The latter combination creates a projection of these rays so that the collimated beam reflected at angles within the scanned range is focused onto a second linear minor part D2 of the detector area, separated from the detector area used for real image monitoring, so that each angle of reflectance corresponds to a specific detector position within this detector area. That is, the second part of the objective has its back focal plane positioned at the plane of the photodetector array. The letters a, b and c at the detector array D2 indicate the positions on the back focal plane of the focused beams a', b' and c', respectively, which exit the prism Pr, the three different angles sequentially illuminating the whole sensor surface and representing three different successive angles of the incident light beam.

The meridian bifocal imaging system described above (one focal length for monitoring the real image, another focal length for monitoring the angle of incidence) enables a simultaneous monitoring of both the position of a reaction site within the sensor area (real imaging), and of the quantitative measure of the amount of reacting species (analytes) at the site, by use of the same detector array.

In FIGS. 1 and 2, the inclined detector plane and the inclined coupling prism exit (non-orthogonal ray-passage at the exit of the prism) indicate the principle, known to anyone skilled in art, to reduce the defocusing of the image at inclined imaging.

As already mentioned above, the coupling prism Pr may be replaced by a coupling grating (see, e.g., WO 88/07202 and PCT/GB91/01573).

A more detailed description of the coupling prism, sensor surface, and bifocal imaging system for a combined image- and angle monitoring at the same detector array is shown in FIGS. 3 to 10.

Figure 3:
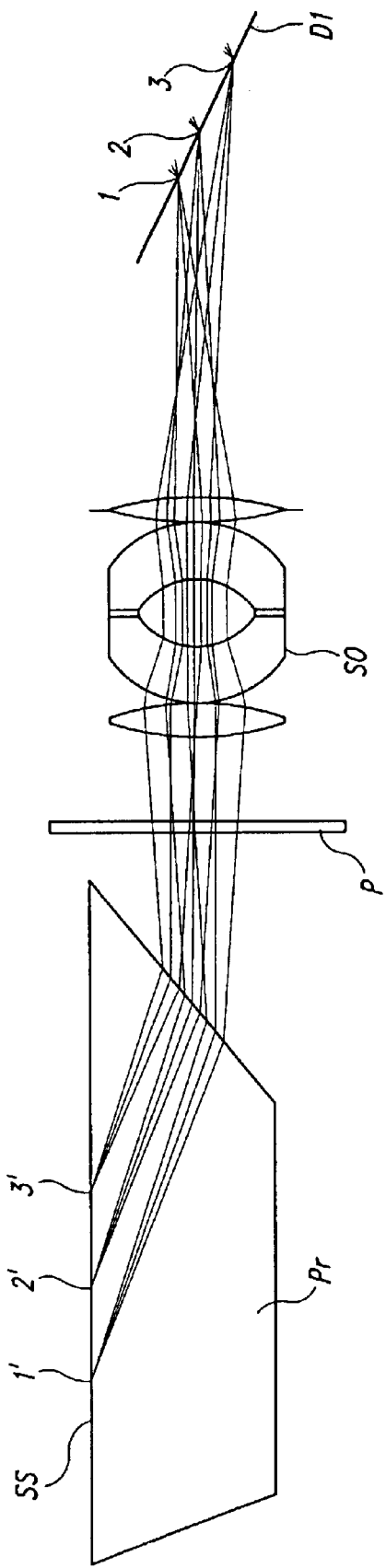
FIG. 3 is a schematic enlarged meridian view of a part of the embodiment shown in FIG. 1.

FIG. 3 (which corresponds to FIG. 1) shows a meridian section of ray bundles reflected at different points or sensor zone heights of the sensor surface, indicated at 1', 2' and 3'. Sensor zone heights 1', 2' and 3' are sharply imaged by the spherical objective SO at meridional heights 1, 2 and 3 on the real image plane on the detector array. For these rays passing only the spherical objective SO, the detector plane is positioned at the real image plane of the lens system.

Figure 4:
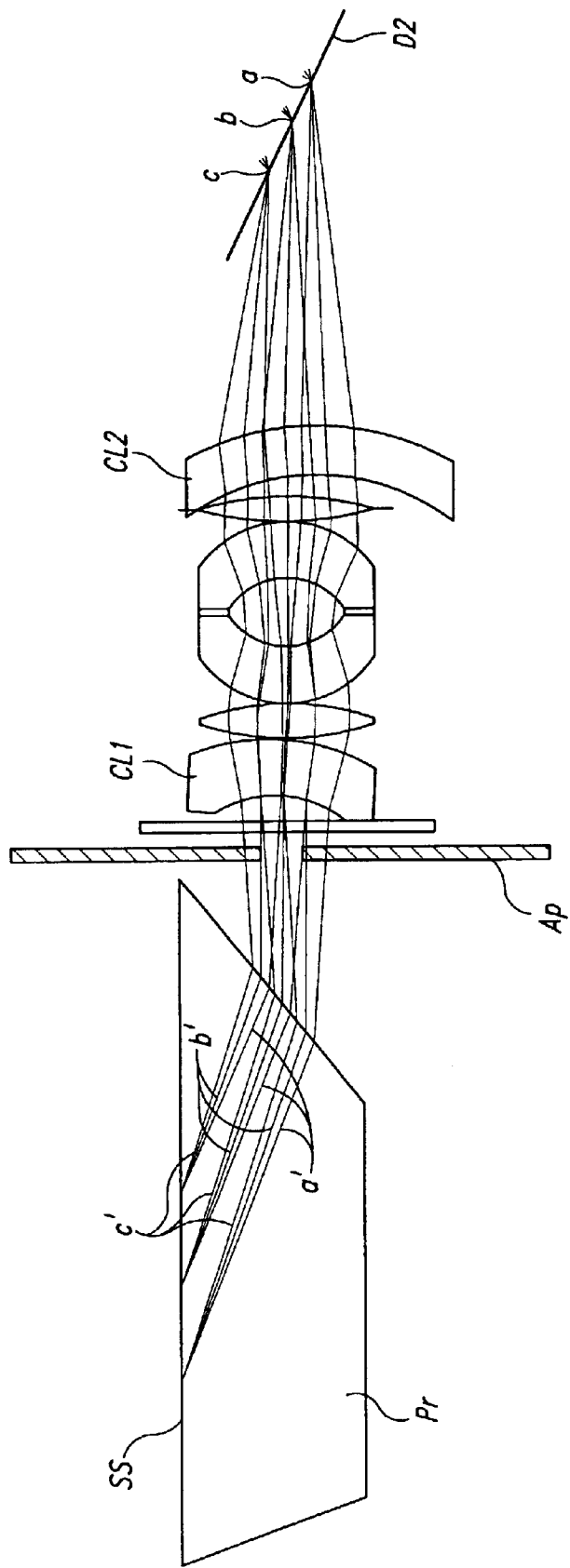
FIG. 4 is a schematic enlarged meridian view of a part of the embodiment shown in FIG. 2.
Figure 5:
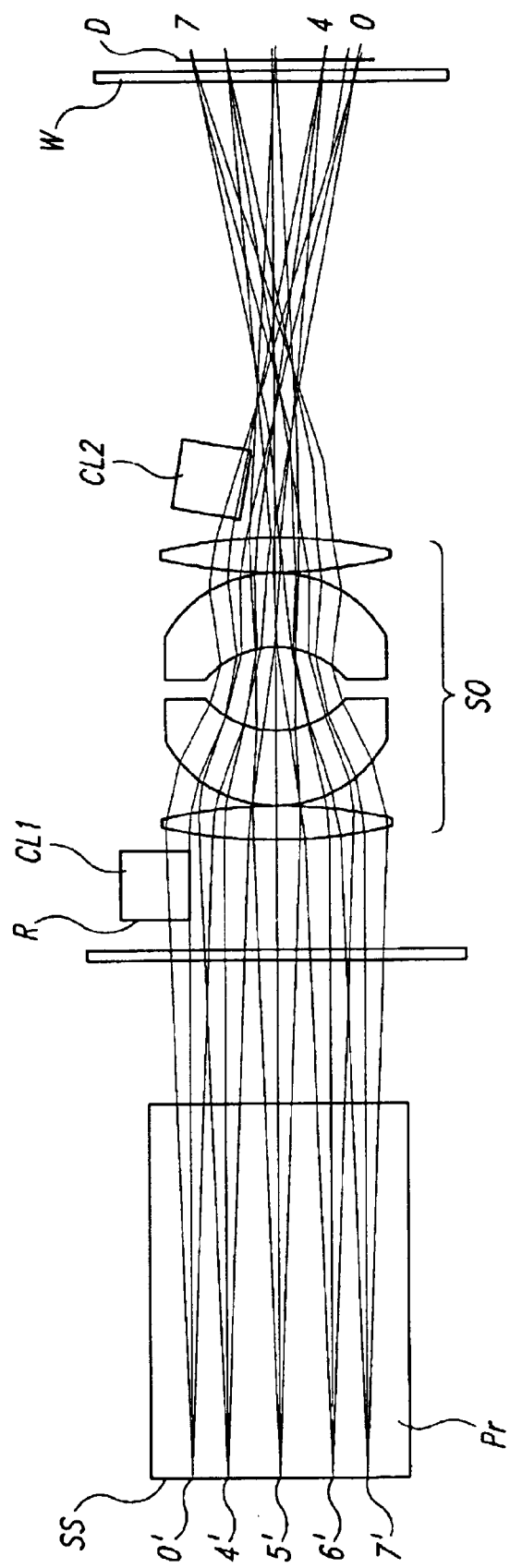
FIG. 5 is a schematic enlarged sagittal view of a part of the embodiment shown in FIG. 2.

FIG. 4 (which corresponds to FIG. 2) shows a meridian section of ray bundles reflected at different angles a', b', and c', at the sensor surface sagittal height 0' (see FIG. 5). Rays reflected at each specific angle are sharply focused to a line at meridional positions a, b, and c, on the detector D2, by the combined spherical objective and cylindrical elements. For a specific angle of incidence of the collimated light, all the rays will be focused to a line across the columns of detector element designated to angular monitoring. By determining the position of this light intensity peak along such a column, using a suitable algorithm and an angular calibration procedure, a real-time measurement of the angle of incidence for the related sensor surface 2-dimensional image is enabled with high resolution, accuracy and speed.

Depending on the chosen angular range, an aperture stop, Ap, may be used to select the rays, and thereby the length along the surface sagittal height 0', required for angular detection.

By introducing an obscuration in a part of the collimated beam, an aperture can be formed in the obscuration for passing of rays used for monitoring of angle of incidence, whereby the width and length of the focused spot or line of these rays at the back focal plane can be suitably adjusted in relation to the size of the pixel and the pixel-separation in the pixel-array of the photodetector, or in the case of a spot-position sensitive large area sensor, in relation to its area. As such, the number of pixels, or the area of the photodetector, covered by the spot-intensity peak-width can be optimized for providing a high spot-position resolution, enabling a high sensitivity of measured angle of incidence. As described in FIGS. 2, 4 and 5, this collimated beam passing the aperture is internally reflected at 0', passes lenses CL1 and CL2, and meets the detector plane D2 at 0.

The obscuration may be made of any mainly non-transparent material of suitable opto-mechanical properties. The obscuration may be positioned at or within the illumination system, or between the illumination system and the first scanning component. In a preferred embodiment, said obscuration is positioned at the interference filter I, as illustrated in FIG. 23.

The aperture is an unobscured opening, taking the shape of a circle, quadrate, or rectangle. The aperture may be positioned either within, or at the edge of the obscuration.

Figure 23:
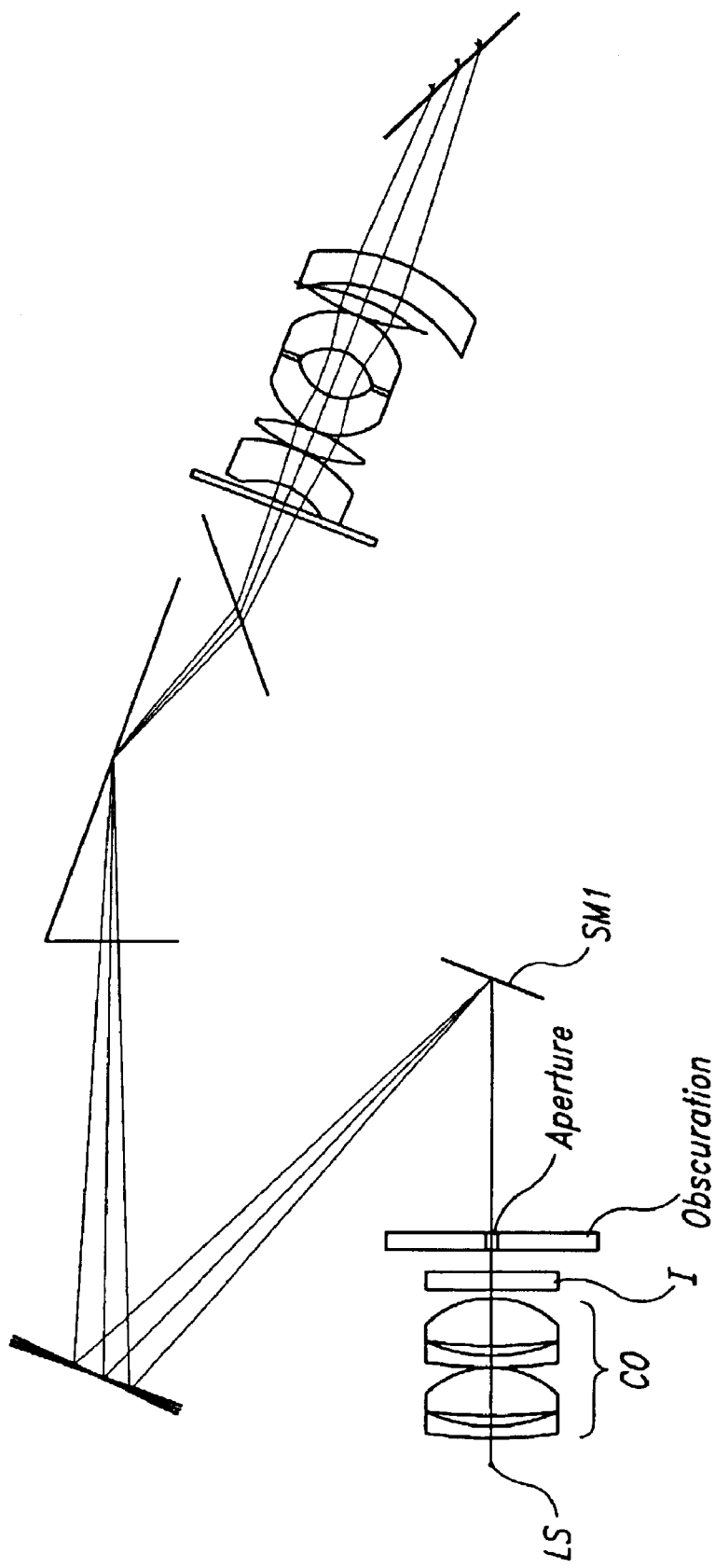
FIG. 23 is a schematic meridian view of a modified design of the embodiment shown in FIG. 2.

In a preferred embodiment, the aperture is co-centric with the center of the illumination system in the plane of incidence, as shown in FIG. 23, while having its center decentered in relation to the illumination system in the direction orthogonal to the plane of incidence, so that the obscuration covers a minor area of the collimated beam that leaves the lens system CO, and the image of the obscuration covers 2–10% of the common photodetector area.

The aperture, has a typical width, in the direction of the plane of incidence, ranging from 0.05–1 mm, a preferred width being 0.2–0.5 mm. In case of the aperture taking the form of a rectangular slit, the slit length is typically within 0.5–3 mm, a preferred length being 1–2 mm.

A suitable masking of the sensor surface at sagittal height 0' to limit the reflection area, and/or a suitable structure that always gives total reflection at the sagittal height part 0' of the sensor surface may be used to obtain the necessary stability of the intensity peak used for angle determination. This may, for example, be accomplished by a sensor surface which in addition to reactant zones also comprises a part (0') which exhibits a mainly constant reflectance independently of incident angle and wavelength and which thus, in for example SPR, does not give rise to a resonance.

A sagittal section of ray bundles reflected at different parts of the sensor surface is illustrated in FIG. 5. Sensor zone heights 4', 5', 6', and 7' are sharply imaged by the spherical objective at sagittal heights 4, 5, 6, and 7 at the detector plane, D, while rays reflected at sagittal height 0' also pass two cylindrical lens elements, CL1 and CL2, which create a defocused intersection of the rays at the detector plane at sagittal position 0. A detector window is indicated at W.

The two cylindrical lens elements may, in the sagittal plane, have a suitable radius, R, providing a refraction in order to locate the image plane of the rays in front of the detector plane, thereby creating a defocusing of the rays across several detector columns used for the angular detection.

Figure 6:
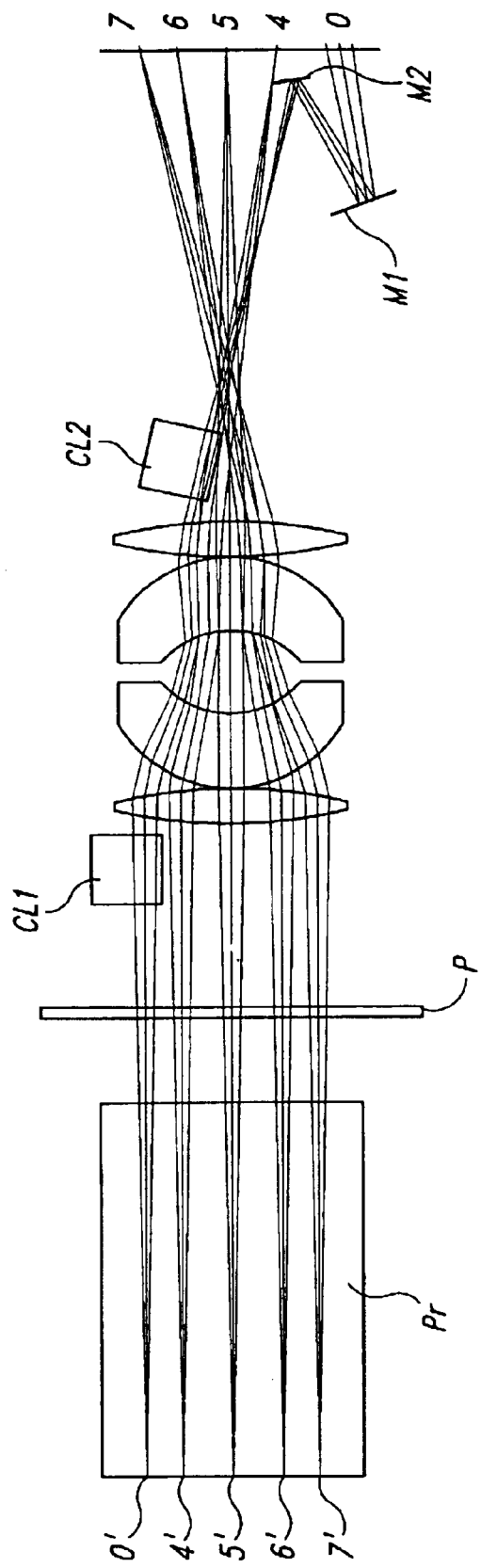
FIG. 6 is a schematic sagittal view of a modified design of the embodiment shown in FIG. 5.

FIG. 6 shows a sagittal section of an alternative optical system design, wherein the rays used for measuring the angle of incidence are given a suitable ray path folding via two fixed mirrors M1 and M2.

Figure 7:
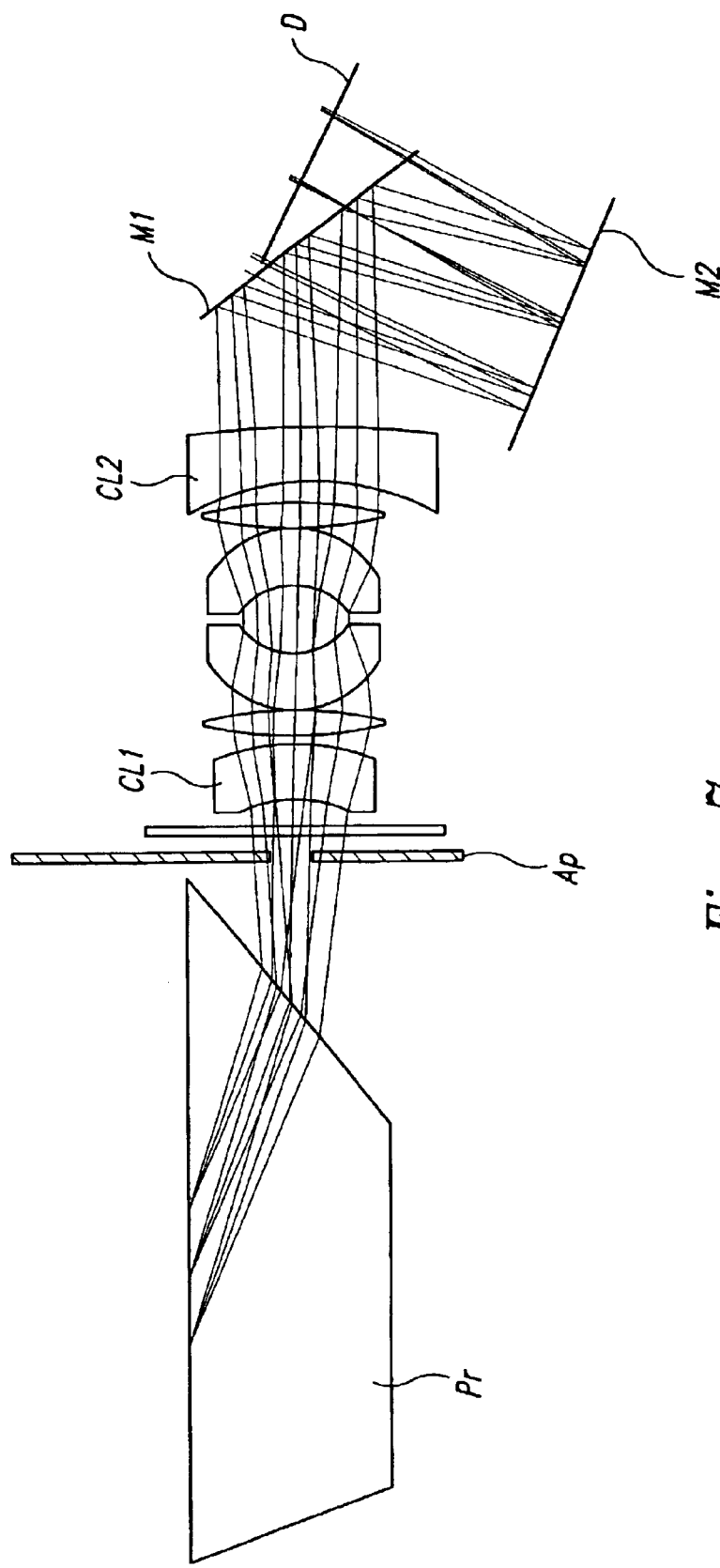
FIG. 7 is a schematic meridian view of the embodiment shown in FIG. 6.

FIG. 7 shows a meridian section of another optical design, similar to that in FIG. 6, which provides for the ray path folding via two fixed mirrors M1 and M2 in order to obtain a required degree of overlap of the back focal plane and the detector plane within a large angular dynamic range.

Figure 8:
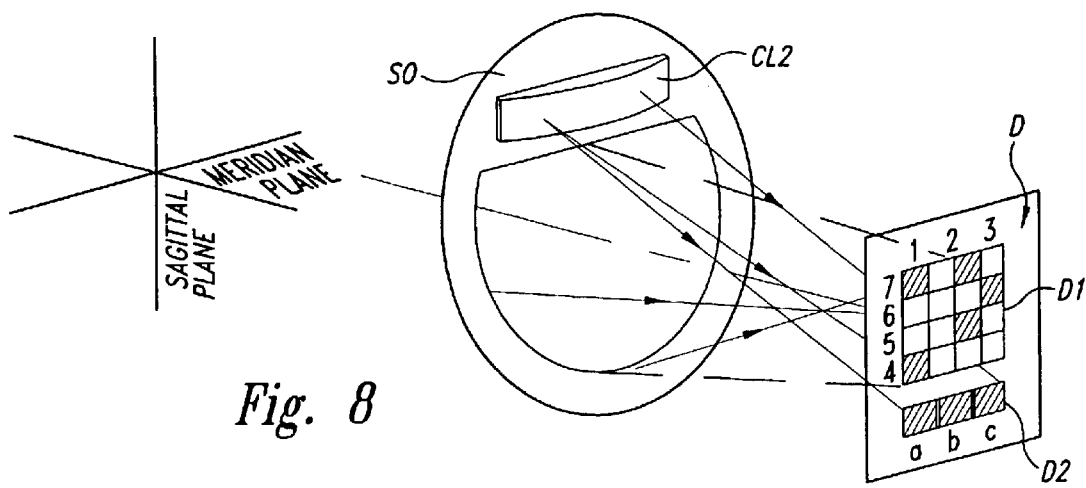
FIG. 8 is a schematic perspective view of the embodiment shown in FIGS. 3, 4 and 5.
Figure 9:
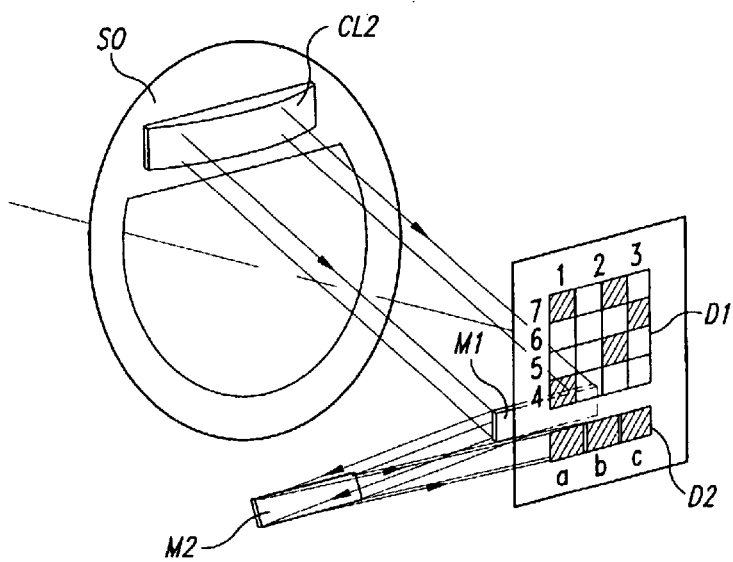
FIG. 9 is a schematic perspective view of the embodiment shown in FIG. 6.
Figure 10:
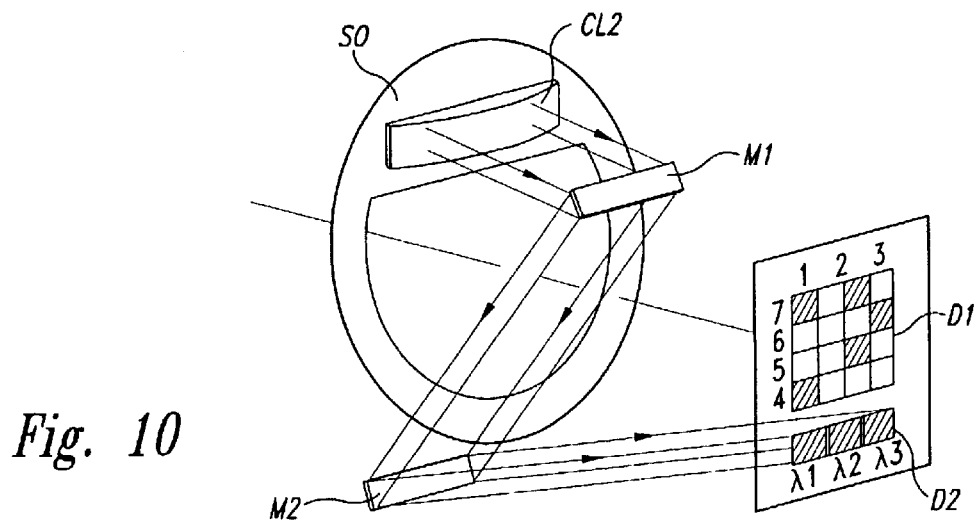
FIG. 10 is a schematic perspective view of a modified design of the embodiment shown in FIG. 7.

The objective and detector design shown in FIGS. 3 to 5 is schematically represented in a perspective view in FIG. 8. Corresponding (schematic) perspective views of the designs shown in FIGS. 6 and 7 are illustrated in FIGS. 9 and 10, respectively. Thus, the optical function of monitoring both the real image and the angle of incidence at the same detector array, by use of the above-mentioned first and second parts of the objective, respectively, is depicted in FIG. 8, whereas FIG. 9 depicts the beam deflection by the folding mirrors M1 and M2 in accordance with the design shown in sagittal view in FIG. 6, and in meridian view in FIG. 7.

Figure 11:
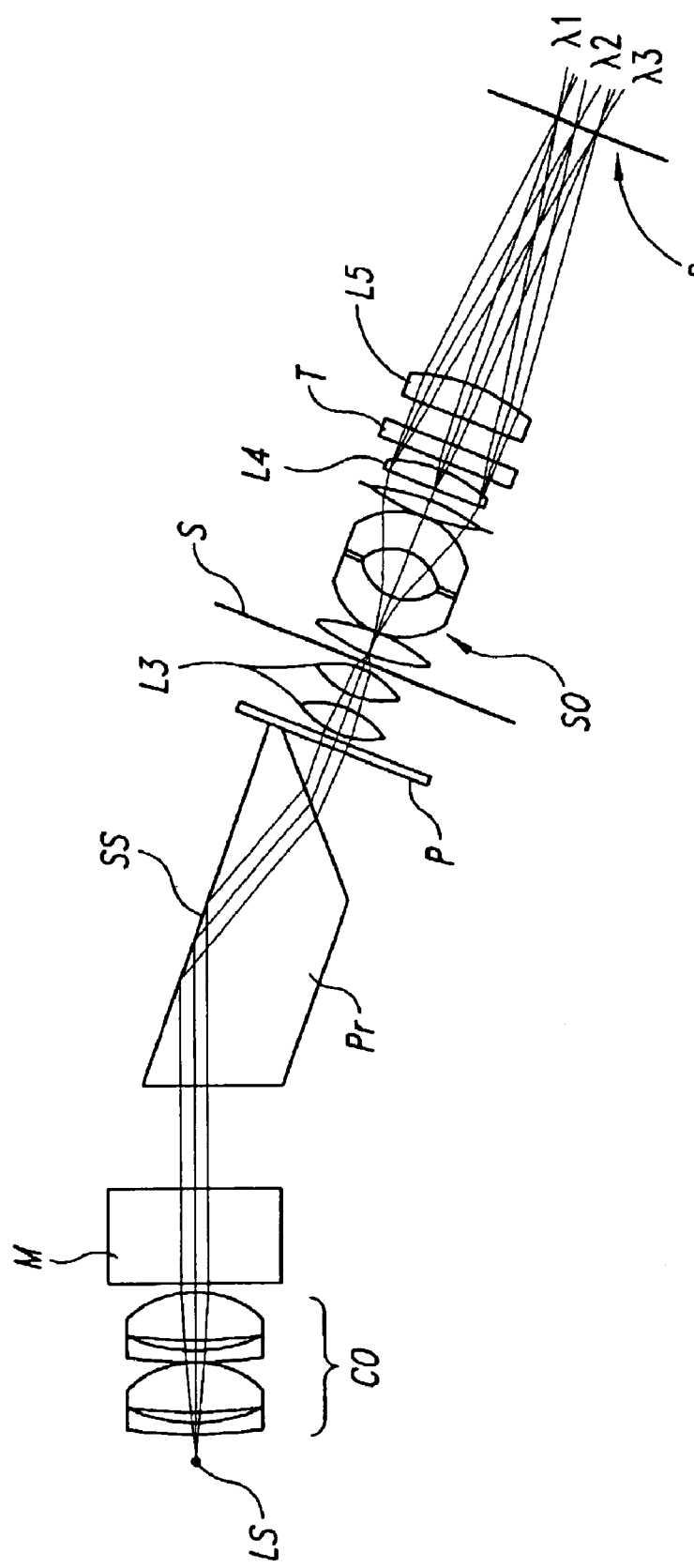
FIG. 11 is a schematic exploded view of an alternative embodiment of an optical sensor apparatus and light ray paths thereof according to the present invention, which embodiment is based on scanning of the wavelength of the incident light.

An alternative optical biosensor system according to the present invention based upon wavelength scanning rather than scanning of the incident light angle is shown in FIG. 11. To this end the system comprises a scanning monochromator light source, and a wavelength monitoring device.

As previously, the biosensor system comprises a light source, LS, and a collimator optics, CO, to produce a parallel beam, which passes a monochromator, M, and is then directed into a coupling prism Pr (grating coupling is also possible). The collimated beam at a fixed angle of incidence is totally internally reflected at the sensor interface side of the coupling prism. The p-polarized component of the beam then passes a polarizer, P, and is cylindrically focused by lenses, L3 onto a slit, S.

As in the embodiments based on angular scanning above, a minor part of the beam is directed into the minor part of an objective, which minor part consists of a spherical objective, SO, combined with cylindrical lenses, L3 and L4, which create a collimated beam impinging on a transmission grating, T.

The light beam is then dispersed by the grating T so that the direction of propagation of the collimated beam depends upon its wavelength. This beam is then brought to a focus by a cylindrical lens, L5 (alternatively, a mirror in a folded configuration), so that for a scanned wavelength, a spectrum consisting of a series of monochromatic images, λ1, λ2, and λ3 of the entrance slit S is obtained at the above-mentioned linear minor area part of a two-dimensional detector array, D2, so that each reflected wavelength corresponds to a specific detector position within this detector area.

For a specific wavelength of incidence of the collimated light, all the dispersed rays will be focused to a line across the columns of detector elements designated to wavelength monitoring. By determining the position of the light intensity peak along such a column, using a suitable algorithm and a wavelength calibration procedure, a real-time measurement of the wavelength of incidence for the related sensor surface (2-D) image is enabled with high accuracy and sensitivity.

As described above for the embodiments using angular scan, one may use a suitable masking at one side of the sensor surface (0' in FIG. 13) to limit the reflection area, and/or a suitable, always totally reflecting structure at that sensor surface part to obtain a necessary constancy of the intensity peak used for wavelength determination.

In accordance with the description above for the embodiments using angular scanning, one may also introduce an obscuration in a part of the collimated beam, wherein an aperture can be formed in the obscuration for passing of rays used for monitoring of wavelength of incidence, whereby the width and length of the focused line at the back focal plane of these rays can be suitably adjusted in relation to the size of the pixel and the pixel-separation in the pixel-array of the photodetector, or in the case of a spot-position sensitive large area sensor, in relation to its area. As such, the number of pixels, or the area of the photodetector, covered by the spot-intensity peak-width can be optimized for providing a high spot-position resolution, enabling a high sensitivity of measured wavelength of incidence.

Figure 13:
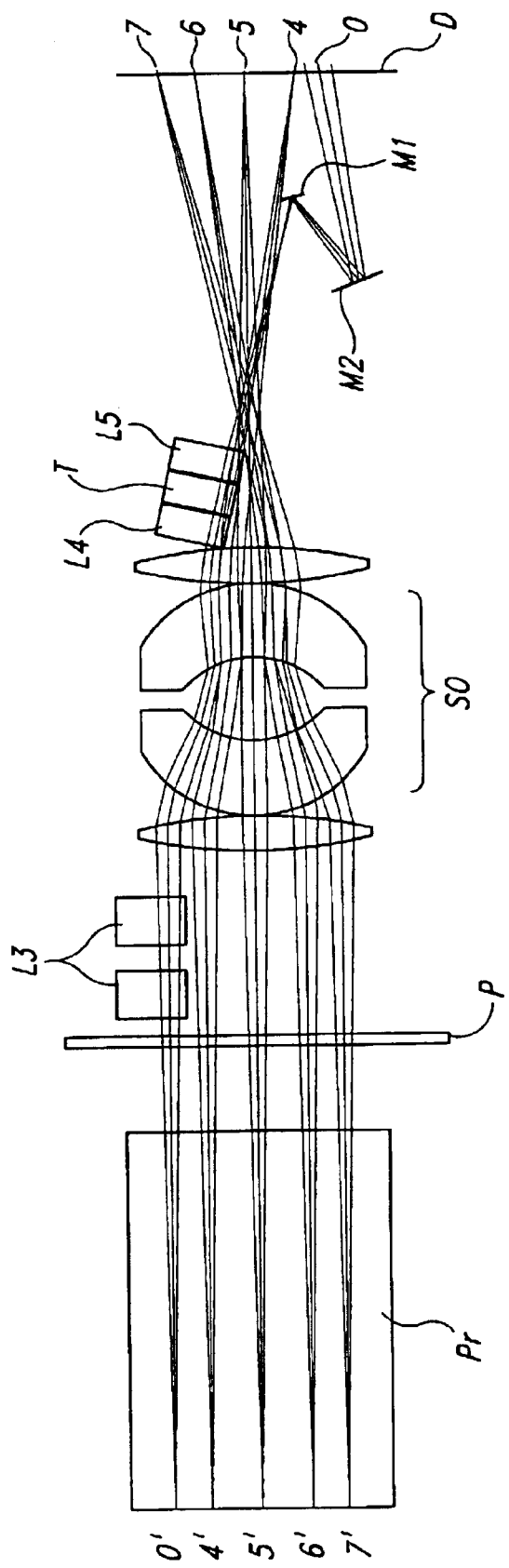
FIG. 13 a schematic sagittal view of the embodiment shown in FIG. 12.

As described in FIG. 13, the collimated beam passing the aperture is internally reflected at 0', passes lenses L3, L4, and L5, and grating T, reaching the detector plane at 0.

Figure 12:
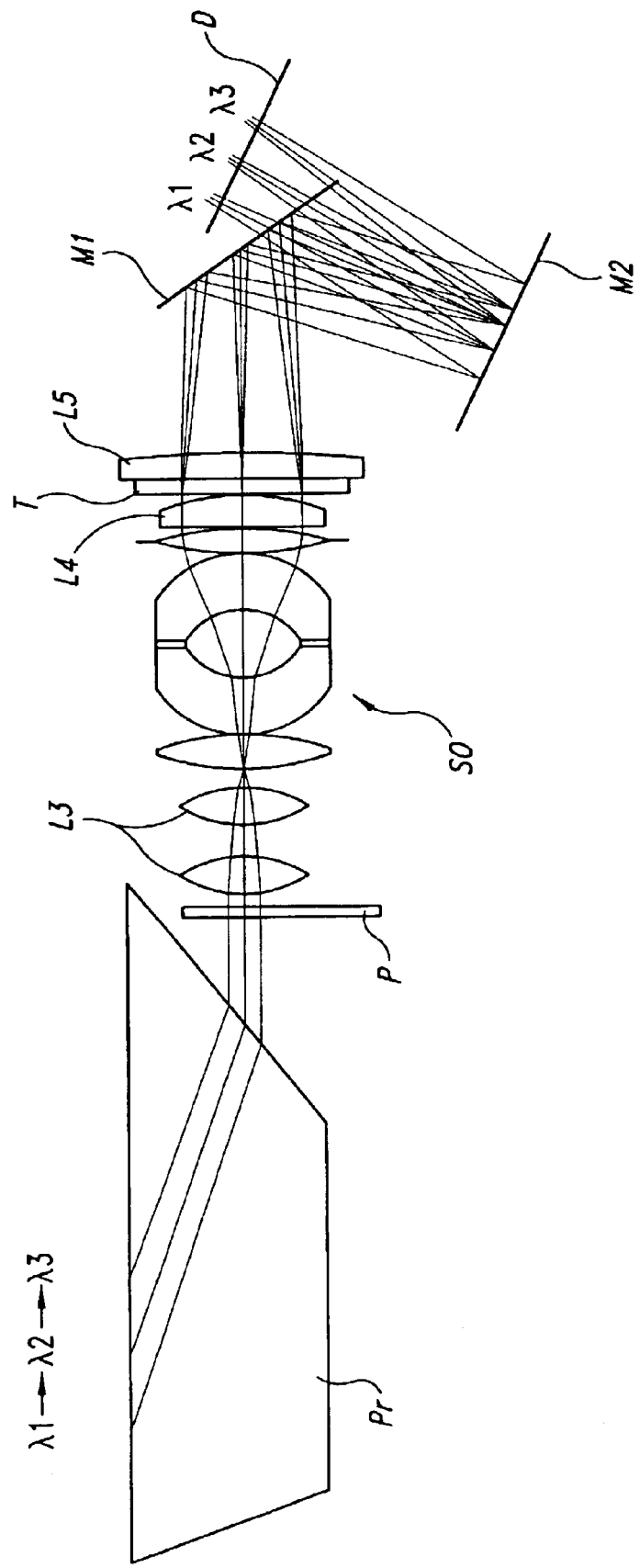
FIG. 12 is a schematic enlarged meridian view of a part of a modified version of the embodiment shown in FIG. 11.

The above-described wavelength monitoring construction is illustrated in more detail in FIG. 12, which shows a meridian section of ray bundles reflected at a fixed angle at the sensor surface. While in the illustrated case, the dispersive element is a transmission grating, T, it may also be a prism. Rays at each specific wavelength λ1, λ2 and λ3, are collimated by the spherical objective, SO, in combination with the cylindrical elements, L3 and L4, diffracted by the grating, T, and sharply focused by another cylindrical lens, L5, to a line at meridional positions λ1, λ2, and λ3, on the detector, D, via folding mirrors, M1 and M2.

The dispersive element may be in the form of a focusing reflective grating, positioned at M1 or M2, in a design replacing the equivalently functioning transmission grating T and focusing lens L5 in FIG. 12.

FIG. 13 shows a sagittal section of ray bundles reflected at different parts of the sensor surface, sensor zone positions 4', 5', 6', and 7' being sharply imaged by the spherical objective, SO, at sagittal positions 4, 5, 6, and 7 at the detector plane, while rays reflected at sensor zone position 0' also pass two cylindrical lens elements, L3 and L4, creating a collimated beam incident on the transmission grating, T. The light beam then passes a cylindrical lens, L5, which focuses the diffracted light in the meridional plane, but defocuses it slightly at the ray-detector plane intersection at sagittal height 0. For the rays passing only the spherical objective SO, the detector plane is positioned at the real image plane of the lens system.

Figure 14:
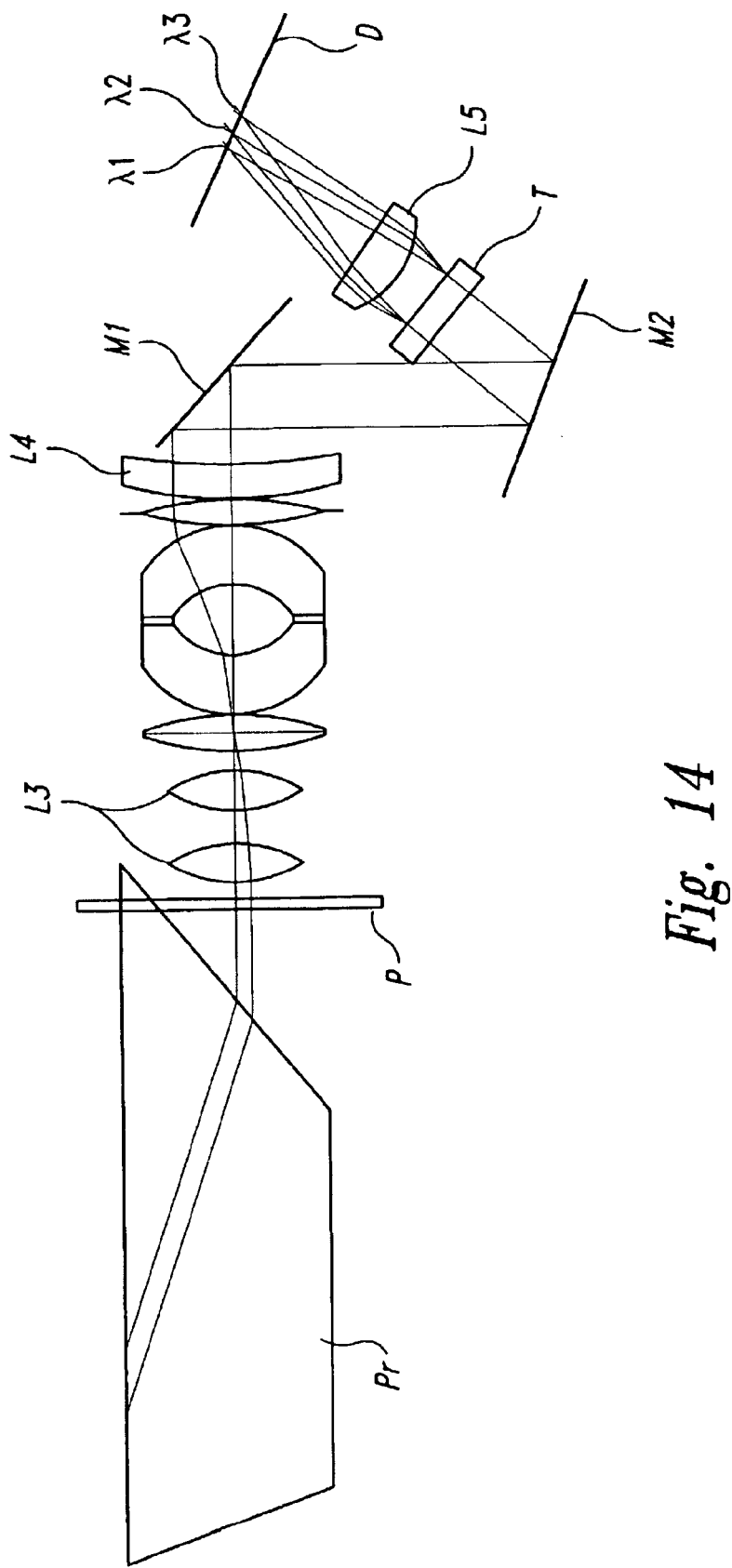
FIG. 14 is a schematic meridian view of an alternative embodiment to that shown in FIGS. 12 and 13.
Figure 15:
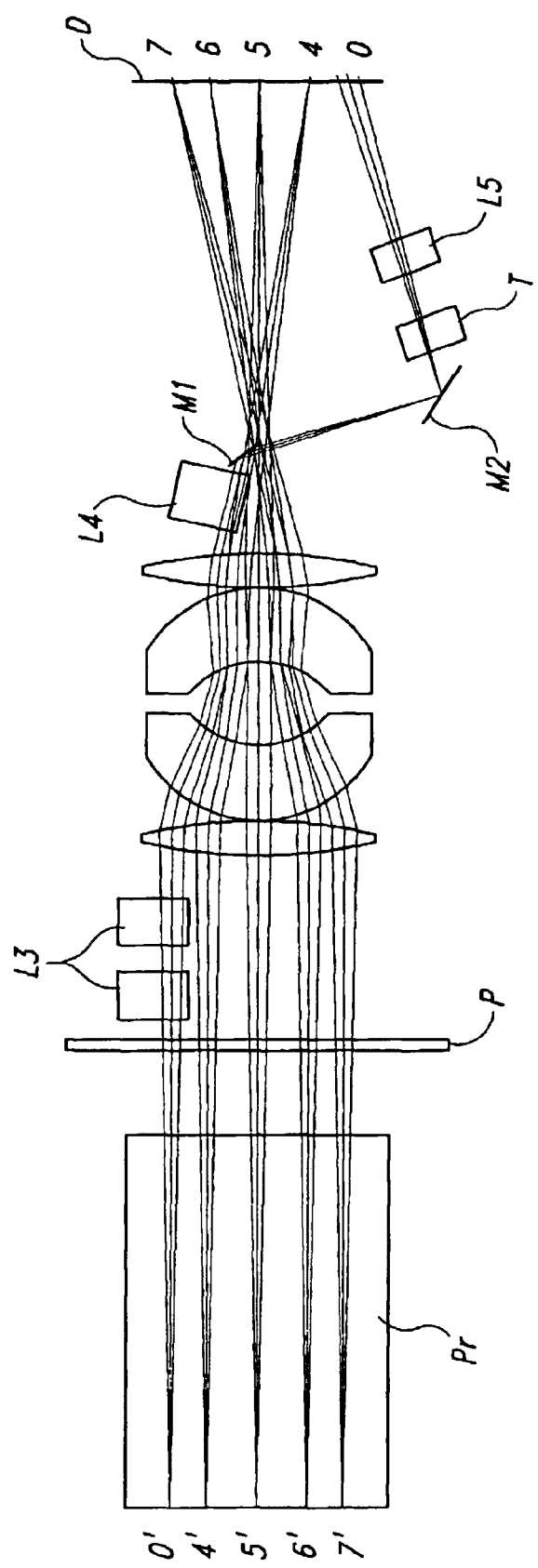
FIG. 15 is a schematic sagittal view of the embodiment shown in FIG. 14.

An alternative embodiment is shown in FIGS. 14 (meridional view) and 15 (sagittal view), where the collimated beam is deflected by first and second mirrors, M1 and M2, and then passes the dispersive element, here a transmission grating, T, followed by the focusing lens, L5.

Figure 16:
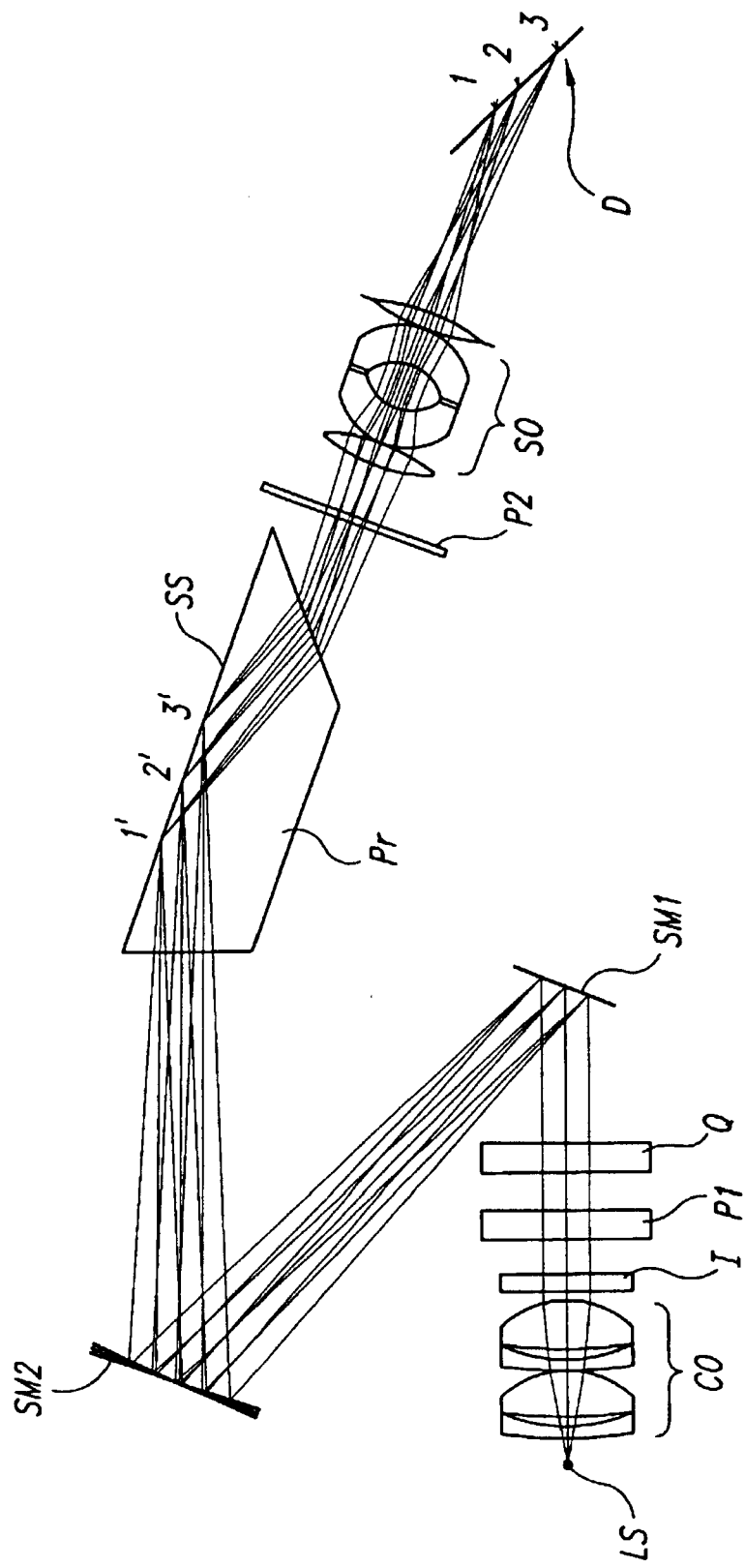
FIG. 16 is a schematic exploded meridian view of an alternative embodiment of the present invention based on ellipsometry.
Figure 17:
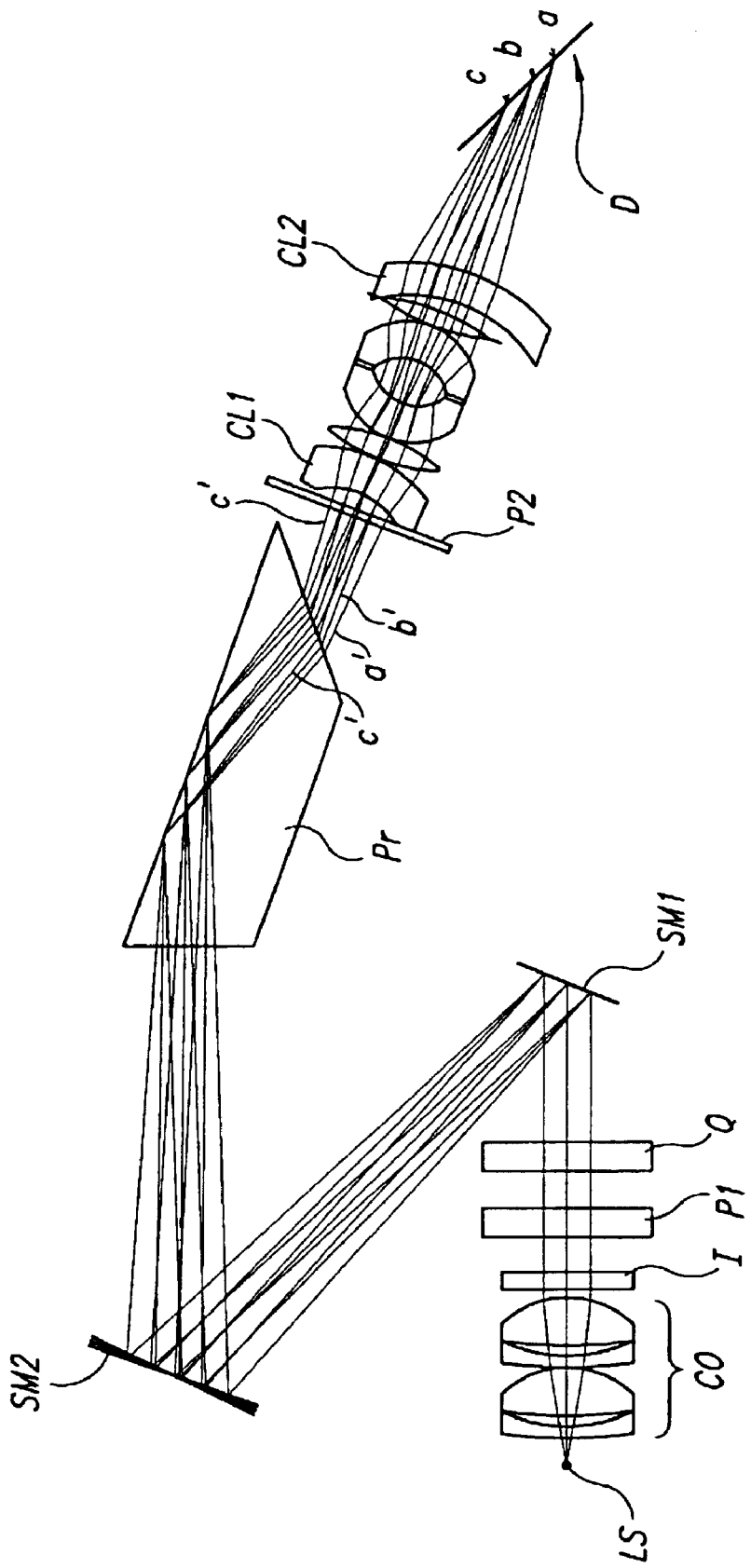
FIG. 17 is another, parallel schematic meridian view of the embodiment shown in FIG. 16.

FIGS. 16 and 17 show an alternative embodiment of the optical biosensor system for ellipsometry. The specific ellipsometer components are shown as a typical ellipsometric set-up, and other ellipsometer configurations are obvious to a person skilled in art.

With reference first to FIG. 16, the illustrated biosensor system comprises a light source, LS, and a collimator optics, CO, to produce a parallel beam. The latter passes an interference filter, I, and then, as a monochromatic beam, passes a first linear polarizer, P1. The s-component of the this linearly polarized light is then retarded by a quarter-wave plate, Q, below called compensator, which creates an elliptically polarized light beam, impinging on a first flat scanner mirror, SM1. Minor SM1 deflects the beam onto a second scanning mirror, SM2, which in turn deflects the beam into a coupling prism, Pr (as before, grating coupling is also possible). The beam is totally internally reflected at the sensor interface side of the coupling prism, and then passes a second polarizer, P2, below called analyzer. A main first part of the beam is directed into a first main part of an objective consisting of a spherical objective, SO, producing a real image on a first rectangular main area part of a detector array, D, of the light intensity reflected from the sensor area.

In an alternative embodiment, the linear polarizer P1 followed by the compensator are positioned between the mirror SM2 and the prism Pr. For a suitable rotation of both the polarizer and analyzer, at a suitable set-up of orientation of the compensator, angle and wavelength of incidence, the light reflected from a sensor zone can be extinguished. Upon a change in the refractive index or thickness of the sample in the zone, the extinction can be followed by scanning the angle and/or wavelength of incidence.

FIG. 17 shows a meridian view of the optical biosensor system, parallel to the view in FIG. 16. Here the ray path for a second, minor part of the beam is directed into a second, minor part of the objective consisting of the spherical objective, SO, combined with two cylindrical lenses, CL1 and CL2. This lens combination creates a projection of these rays so that the collimated beam reflected at different angles, here represented by beams a', b' and c', within the scanned range is focused onto a second linear minor part of the detector area, at a, b and c, respectively, this detector area being separated from the detector area used for real image monitoring, so that each angle of reflectance will correspond to a specific detector position within this detector area. Thus, the above-mentioned second part of the objective has its back focal plane positioned at the plane of the photodetector array.

The above described meridian bifocal imaging system in combination with an ellipsometer provides a simultaneous monitoring of both the position of a reaction site within the sensor area (real imaging), and of the quantitative measure of the amount of reacting species at the site, via at least one of the angle or wavelength of incidence, by use of the same detector array.

From the above description of exemplary optical system designs embodying the present invention it is readily seen that monitoring the actual change of at least one of the angle and wavelength of incidence via the bifocal imaging represents a considerable advantage in relation to the prior art in that the need to derive this change from any steering signal driving the angle scanner or scanning monochromator is eliminated. The scanner driver electronics and software thus just have to provide a suitable dynamic range and scan speed for the angle or wavelength.

The above-described optical designs demonstrate the optical function of the present invention. It is, however, readily appreciated by a person skilled in the art, that these optical designs could be optimized to achieve a suitable performance and function of an apparatus constructed based on these designs.

Also, while in the above described optical systems the bifocal (in the meridian plane) imaging system is based on lens optics, it is readily understood that the imaging system may comprise diffractive optical surfaces for improving imaging quality, image plane flatness, and image plane tilt, to match the needs of the photodetector array. Furthermore, diffractive optics may be the main component in the objective which forms the above described real image and angular projection on two separate areas of the same detector array.

In the following, the different parts of apparatus embodying the above-described optical functions will be described in more detail.

Thus, in accordance with the embodiments of FIGS. 1 to 10 described above, the optical construction employs an illumination system comprising a mainly monochromatic light source and a scanning plane mirror system, an optical coupling component (plane sided prism or grating) in optical contact with a sensing surface, an imaging system comprising a bifocal objective and a photodetector matrix array. An algorithm and a computer program are provided which permit an interpretation of the signals from a first main part of the photodetector into a real image of the sensor pattern, and from a second minor part of the photodetector into the angle of incidence of the probing light. The angle of incidence at a specific parameter of the light intensity, e.g., minimum or maximum, for each sensor zone may thus be monitored simultaneously.

For example, the invention permits a beam having a diameter within the range of about 3 mm to 30 mm to be angularly or wavelength scanned and monitored at a resolution of 0.0001 degrees, and 0.002 nm, respectively, within the range of angle or wavelength of interest, wherein the rays are collimated to a required degree (preferably within about 0.002 degrees).

Illumination System

The illumination system creates a collimated beam at a suitable monochromatic wavelength. In the angular scan mode of the invention, the beam is scanned by a plane mirror system creating a collimated beam, the angle of incidence of which at the sensing surface is scanned while the illuminated area at the sensing surface is mainly fixed. In the wavelength scan mode, a wavelength dispersive device in combination with collimator optics create a collimated beam which is incident at the sensing surface at a fixed angle.

The light incident on the total internal reflection interface may be p-polarized or consist of both p- and s-polarized components, i.e., being suitably elliptically polarized.

The light source may be either mainly non-coherent, e.g., a light emitting diode, a tungsten-halogen lamp, or mainly coherent, e.g., a laser diode.

In an apparatus based on angular scanning, the light source may be either mainly monochromatic, e.g., a light emitting diode in combination with an interference filter, or a laser diode, or a light source capable of sequentially emitting a suitable number of wavelengths, one specific wavelength at each angular scan.

In an apparatus based on wavelength scanning, the light source may, e.g., be a white light source, such as a tungsten-halogen lamp, in combination with a scanning wavelength dispersive device. Such a scanning monochromator may be motorized to sequentially emit wavelengths within a wavelength range, which in combination with the collimator creates a collimated beam.

Angle Scanning Means

Fundamentally, scanning devices are light beam deflectors. Deflectors can be categorized into reflective, refractive, and diffractive (acousto-optic scanners, holographic scanners). Scan patterns and scanning motions are inextricably interrelated involving both beam displacement and beam-displacement rate, and beam deflection and beam-deflection rate. Scanning motions essentially fall into three basic movements, rotational, oscillatory, and translational.

The scanning of the angle of incidence with time of a parallel light beam by utilizing a collimated beam deflecting element, may be created by low inertia components, e.g., vibrating or rotating mirrors or a moving grating, or an inertialess acousto-optical deflector.

The beam deflecting system for an angularly scanned imaging consists in a preferred embodiment of mirrors, which as non-refractive optics does not need to be corrected for chromatic aberrations. In a preferred form, two oscillating or rotating inter-related plane mirrors are combined with a plane sided coupling prism, or a grating, which deflects a collimated beam during the angular scan of the beam so that the optical axis of the beam always intersects mainly the same point at the sensor surface (to obtain reduced beam walking, i.e., improved stability of the light intensity which improves the sensitivity of the instrument), and an imaging system designed to create a real image of the sensor surface in combination with a simultaneous projection of the reflected light into an instant measure of the actual angle of incidence.

The incident angle for collimated beams should typically be scanned within an angular range of ±5°, with a detected angular resolution of ≦0.0001°, corresponding to a refractive index resolution of 0.000001. For real-time monitoring, the angular scan should be rapid.

A preferred scanned angular interval is ≈70±6° at a wavelength of 820 nm, alternatively, ≈77±8° at a wavelength of 660 nm.

The bifocal imaging system described above, may be combined with any of the numerous arrangements for angular scanning of a collimated incident beam available in the literature.

A preferred angular scanner comprising two plane mirrors, the turning movements of which are interrelated via the steering electronics, has already been described in connection with FIGS. 1 and 2.

Figure 18:
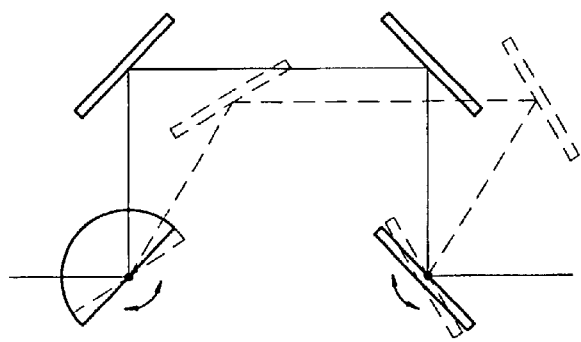
FIGS. 18 to 22 are schematic illustrations of prior art means useful for scanning the angle of incident light in apparatuses of the present invention.

A first alternative scanning principle is the twin parallel-mirror described in Harrick, N. J., Internal Reflection Spectroscopy, Harrick Scientific Corp., 1987, New York, p. 185, and shown in FIG. 18 herein, however, after replacing the convex coupling lens in FIG. 18 with a prism as in the specifically described embodiments of the present invention.

Figure 19:
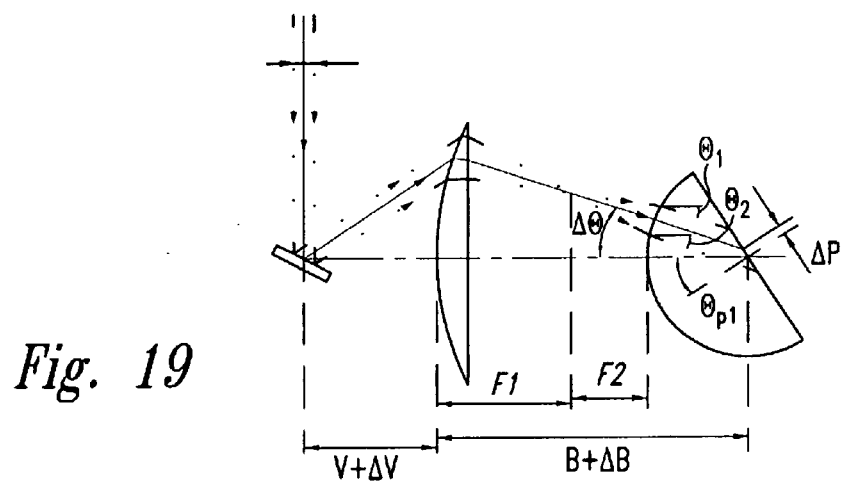
Figure 20:
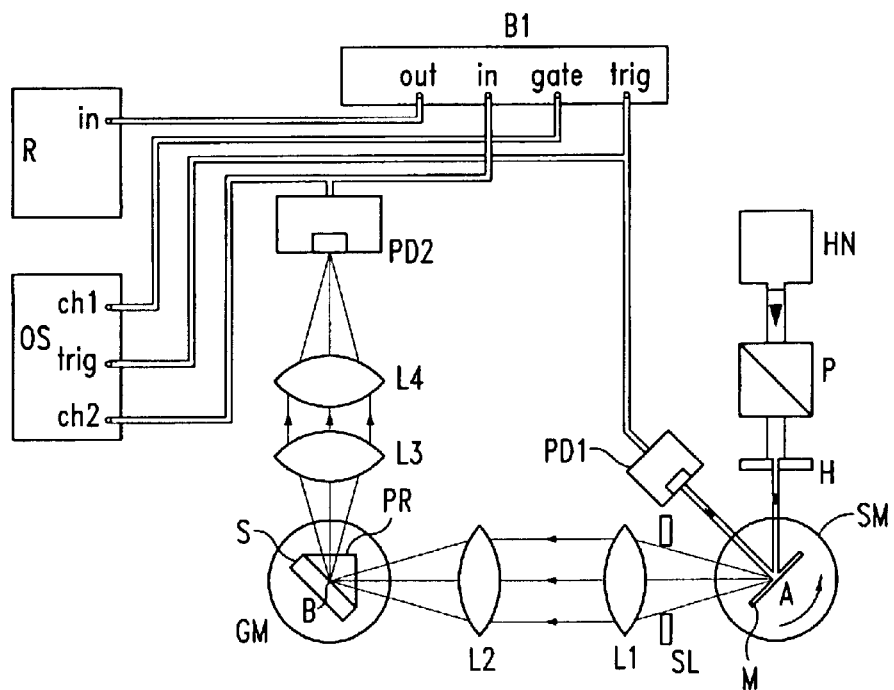

A second alternative scanning principle is an optically optimized (i.e., to obtain overlapping focal surfaces for the whole angular range) system comprising one plane mirror and focal surface flattening optics, in accordance with the scanners described by Lenferink, A. T. M. et al., Sensors and Actuators B, 3 (1991) p. 262, shown in FIG. 19 herein, and Oda, K., et al., Optics Communications, Vol. 59, No. 5, 6, 1986, p. 362, shown in FIG. 20 herein.

Figure 21:
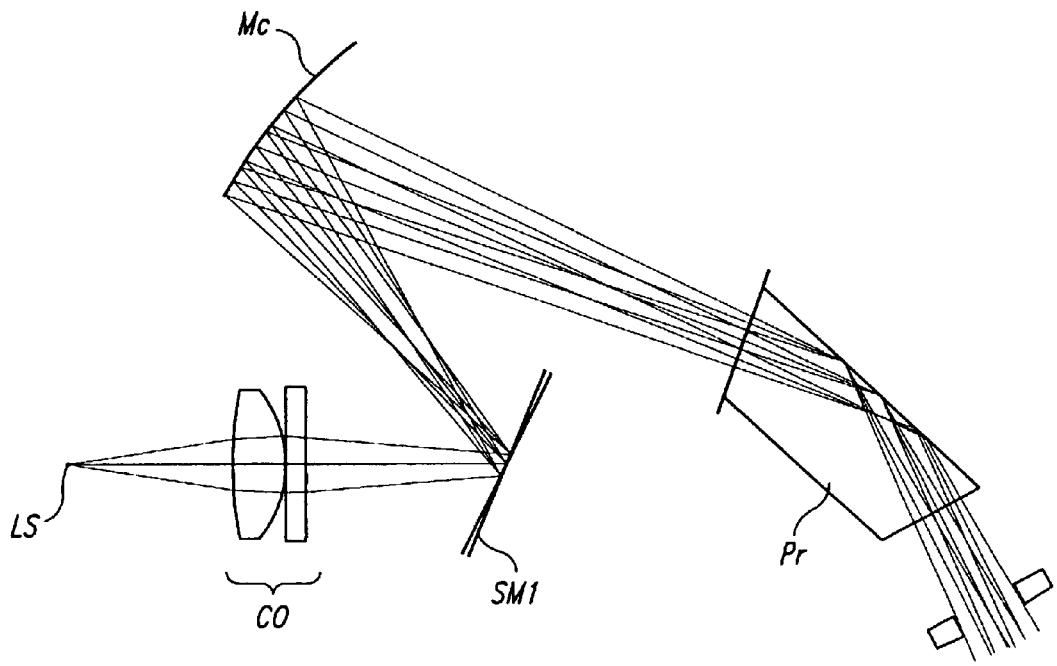

Still another alternative scanning principle, equivalent to the previous one for focal surface flattening optics, consists of a plane mirror, SM1, scanning a focused beam from the illumination source, LS, along a focal surface of a concave mirror, Mc, creating an angle scanned collimated beam, as shown in FIG. 21. This may also be described as that the illumination system includes one oscillating/or rotating plane mirror in combination with a concave cylindrical mirror, which deflects a focused beam during the angular scan of the beam so that its focal surface overlaps the focal surface of the cylindrical mirror, thereby creating a scanning collimated beam.

Figure 22:
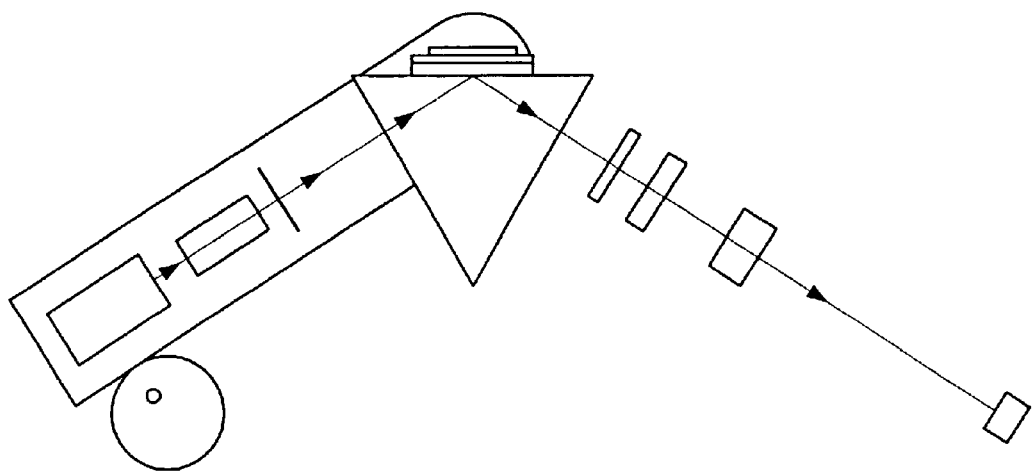

Still another alternative scanning principle comprises a pivotally moving illumination system, e.g., such as that described in WO 93/14392, and shown in FIG. 22 herein.

Still another possible scanning structure is an excentric rotating polygonic scanner, replacing the cooperating mirrors SM1 and SM2 in FIGS. 1 and 2. Typically, such a polygonic scanner consists of eight planar mirrors mounted on the periphery of a rotating wheel.

Wavelength Scanning Means

When the reflectometry in the method and apparatus of the present invention is performed as a function of the incident wavelength at a fixed angle, the light source is combined with a scanning monochromator which in combination with the real imaging and image detection sequentially creates a series of images, each of a specific wavelength. A smaller part of the same image detector (or a separate detector) is used for measuring the wavelength. For this dual detector function to be possible, this smaller detector part is combined with a wavelength dispersive element, which spatially separates light at different wavelengths.

The incident wavelength should typically be scanned within a wavelength range of ±200 nm, with a detected wavelength resolution of ≦0.002 nm, corresponding to a refractive index resolution of 0.000001.

In its simplest form, the dispersive element consists of a prism. Due to the refraction of the light in the prism, the rays must be deflected by, e.g., a reflective element, in order to reach the detector.

A grating spectrograph is similar to a prism spectrograph. The light to be analyzed passes first through a combination of a slit and a collimating lens. It then reaches the reflecting or transmission grating, set with its grooves parallel to the slit, where light of different wavelengths is diffracted at different angles, and is for each order drawn out into a spectrum. A second lens focuses these diffracted rays onto the detector array. A grating with a high groove density per unit width may give a few orders, but their spectra are spread out much wider than those formed by a lower density.

Generally, as is understood by the skilled person, the bifocal imaging system described above with the specific embodiments of the biosensor system of the invention may be combined with numerous arrangements for scanning monochromators available in the literature.

Sensor Surface and Opto-Coupling to the Collimated Beam

In a preferred embodiment, the collimated light impinges on the interface between sensor surface substrate and the actual sensor surface under total internal reflection conditions. The substrate/sensor surface may be a separate exchangeable component consisting of a sensing layer coating a transparent substrate, e.g., of glass or plastic, that is in optical contact with the optical coupling media described above. The substrate should be matched in respect of refractive index to a coupling prism that transmits the light beams of the illumination system to the sensor surface. Alternatively, a plane side of the coupling prism may be the substrate.

According to an alternative opto-coupling principle, the substrate may be in the form of a grating on either the sensor surface substrate interface, or on the opposite side to this interface on the substrate.

When, for example, the detection principle is based on SPR, the sensor surface comprises a plasmon-active material, such as gold or silver. In the case of internal Brewster angle detection, on the other hand, the sensor surface is of a transparent material, i.e., there is no metal film.

The sensor surface part at the sensor surface plane that provides the light for the detection of angle or wavelength should have a low variation in reflectance for the scanned angle/wavelength range. A varying light intensity during the scan mode of the invention, e.g., as caused by SPR also within this part of the detected light, is likely to disturb the accuracy of the angular determination. It is therefore preferred to use for the angle/wavelength measurement a part of the sensor surface that is not brought in contact with the sample, e.g., a part in contact with flow cell material in case of a sensor surface docking system of the type described in the aforementioned U.S. Pat. No. 5,313,264. Such a part may be located, e.g., at the flow cell wall, by the software used in the instrument. Thereby, the light intensity of the focused line on the detector will be insensitive to any light interaction with the sample during the angular or wavelength scan.

Alternatively, a purely reflecting part (no evanescent wave) of the sensor chip is used for the measurement of the incident light angle or wavelength to obtain a light beam intensity during the angular or wavelength scan that is not influenced by the sample.

Imaging System

Depending on the choice of microscopy monitoring or degree of large area monitoring, the person skilled in art may design a suitable imaging system.

In the case of angular scanning, for each specific incident angle the reflected light is collected by an objective, which images a mainly stationarily illuminated sensor area. A possible marginal walk of the illuminated area is not a problem, provided that it is the stationarily illuminated central part of the illuminated sensor surface that is imaged. The imaging system creates an image in the detector plane where the reflectance minima or maxima correspond to the local distribution of refractive index over the sample area. An optimum light intensity for imaging requires that the main part of the illuminating optical power is localized to the stationarily illuminated and imaging part of the sensor surface.

For microscopy applications, the sensor area is enlarged, typically 20–40×. This image may be detected by a photodetector matrix, e.g., of CCD (charge-coupled device) camera type. Alternatively, this image may be further enlarged by an ocular, typically 10–20×, and projected on the photodetector matrix.

For large area applications, the sensor surface is generally reduced. Typically, a sensor area of, say, 3 cm×3 cm is reduced about 0.3×–0.6× on a conventional CCD-detector.

Two exemplary designs of imaging systems for use in the present invention are given below:

1. An objective of magnification 15× together with a photodetector array with pixel dimensions 15×15 $\mu m^2$, and an array-area of 6×8 $mm^2$, may monitor a total sensor area of approximately 0.4×0.5 $mm^2$ with a lateral resolution of 1×1 $\mu m^2$.
2. An objective of magnification 0.2× with pixel dimensions 15×15 $\mu m^2$, and an array area of 6×8 $mm^2$, may monitor a total sensor area of approximately 3×4 $cm^2$ with a lateral resolution of 75×75 $\mu m^2$.

Image Processing and Monitoring Software

An outline of the requirements on the computer software for the analysis and presentation of the monitored reaction zones is given below.

By the use of non-coherent light, the distribution of totally internally reflected reflectance minima over the sensor surface may be detected in the form of images synchronized to the incident angle of the illuminating light. The image reflectance data and image-related data are processed in real-time in an image processing computer program to provide, for example, a three-dimensional refractometric image with the quantified mass-distribution as a function of sensor surface coordinate.

A high time resolution between the refractometric images requires a short angle-scanning period. A typical commercially interesting frame-rate range is of the order of 50–60 Hz. Each frame of detected intensity corresponds to a specific angle or wavelength. Thus, during one second a number of 50–60 intensity- and angle-data points are read for each of the detector elements corresponding to a sensor zone.

To obtain a suitable mean value for a cluster of detector elements covering a specific sensor zone, the image processing software calculates a reflectance curve for the zone by first averaging the intensity of the chosen elements at each angle or wavelength, and then plots this intensity versus the angle or wavelength. For example, each zone may obtain one reflectance curve per second (i.e., the reflectance curve rate is 1 Hz). A second algorithm calculates the angle or wavelength at the curve parameter correlated to the refractive index within the sampled zone, normally, the minimum reflectance or centroid of the dip in the reflectance curve.

The higher the rate of the sample interaction with the sensor zone, the higher angle and/or wavelength resolution is required, and the higher frame rate will be needed for the image processing.

The real image on a first main part of the matrix detector is read and stored by a so-called frame-grabbing program, while the position of maximum intensity, or alternatively, the centroid of the intensity curve, for the angle- or wavelength-related beams focused on a second minor part of the detector matrix is calculated and stored by a suitable algorithm.

An exemplary measurement/calculation procedure based on the angular scan mode is described below.

First, an initial normalization of reflectance data is performed by measuring total reflectance during an angular scan without sample addition. This procedure may comprise the following steps:

a) Define for each sensor zone a cluster of pixels on the photodetector matrix, including a center pixel and a selected number of neighboring pixels,
b) start a clock for the measurement process,
c) start driving an angle scan over a predetermined angular range (driving is, e.g., stepping or rotational motor control or moving coil current for oscillating mirrors),
d) read from the 2-D image detector part of the photodetector matrix into an image data memory, a sequence of raw data images for averaged 2-D reflectance from the detector pixels corresponding to each sensor surface zone,
e) simultaneously, read from the angle detector pixel row of the photodetector to an angular data memory, a sequence of raw data for the reflectance intensity peak (pixel number, time),
f) calculate for each 2-D image the incident angle from the pixel number of the respective intensity peak on the detector pixel row,
g) store the angle and time for the respective raw data images in an image/angle/time matrix,
h) calculate a normalizing matrix from the measured reflectance values of the 2-D image, the normalized reflectance being identical within the sensor zones for all angles, and
i) store a normalizing matrix (normalizing data, angle).

The system is now ready for monitoring sample surface concentrations at each sensor zone by measuring reflectance minima during the angular scan. Measurements are performed first with only solvent at the surface and then with sample plus solvent. The measurement procedure may comprise the following steps:

a) start a clock for the measurement process,
b) start driving an angle scan over a predetermined angular range,
c) read from the 2-D image detector part of the photodetector matrix into an image data memory, a sequence of raw data for averaged 2-D reflectance images from the detector pixels corresponding to each sensor surface zone,
d) simultaneously read from the angle detector pixel row or rows of the photodetector to an angular data memory, a sequence of raw data for the reflectance intensity peak (pixel number, time), e) calculate for each 2-D image the incident angle from the pixel number of the respective intensity peak on the detector pixel row, f) store the angle and time for the respective images in an image/angle/time matrix, g) calculate a normalized 2-D image from the raw data matrix of the 2-D image by correcting with the respective normalizing matrix, h) store the angle and time for the respective normalized image in a normalized image/angle/time matrix, i) select a specific sensor zone and the corresponding part of the normalized image/angle/time matrix, j) copy data for the angular dependence of the reflectance curve (normalized reflectance, angle), k) calculate from the data in j) the angle and reflectance of the reflectance minimum, l) calculate from the normalized reflectance matrix a medium time for the angular scan ((start time+stop time)/2), m) store a medium time for the reflectance minimum angle (in k)) and the specific sensor zone in a reflectance minimum angle/sensor zone/medium time matrix, n) calculate the reflectance minimum angle shift for the respective sensor zone and time in relation to a reference angle for the sensor zone obtained before the sample reaction therewith, o) calculate from the angle shift the internal surface concentration of the sensor zone, p) store the internal surface concentration in a matrix (surface concentration, medium time), q) select the next specific sensor surface zone and calculate the surface concentration as above, r) calculate a differential surface concentration for selected reference zones, s) store the relative surface concentration in a matrix (differential surface concentration, medium time), t) present simultaneously in graphs or tables the internal and relative surface concentrations, respectively, as a function of time for the respective surface zone, u) start the driving of the next angular scan, and v) repeat the above measuring procedure up to a final analysis time.

The driving of the angle may be continuous and the storing of the image and angle data may be trigged by the angle data scanning over the predetermined angular range. These stored image/angle/time-matrices are shifted into the calculation and presentation procedures at a rate depending on the computer performance.

Instead of measuring and presenting surface concentrations, it is, of course, possible to measure and present surface concentration changes, surface refractive indexes, surface refractive index changes, surface thicknesses and surface thickness changes.

The amounts of sample species bound or adsorbed to the different sensor spots or subzones may be related to each other by analytical software. The time relation of the refractometric images makes it possible to obtain via further image data processing mass distribution kinetic data for, e.g., specific sample binding/desorption, sample displacement along the sensor surface, or for the separation process.

The use of coherent light makes it possible to detect, in addition to the distribution of total internal reflectance minima over the sensor surface, also interferometric changes caused by locally changed mass distributions. Image data processing of the lateral movement pattern of such interference bands may be used to obtain an increased sensitivity to lateral refractive index changes on the sensor surface.

The invention is, of course, not limited to the embodiments described above and shown in the drawings, but many modifications and changes may be made within the scope of the general inventive concept as defined in the following claims.

Experimental Procedure Example

The principle of the present invention was verified as demonstrated in FIGS. 24a–24d, by use of a pivotally moving illumination system similar to the one described in FIG. 22, using a light emitting diode of center-wavelength 766 nm, lenses and a sheet-polarizer providing p-polarized collimated beam of diameter 8 mm, an interference filter of bandwidth 3 nm, an imaging embodiment according to FIGS. 3, 4, and 5, and a CCD-photodetector matrix connected to a video-recorder. The obscuration, imaged as the dark right part in FIGS. 24a–24d covering about 25% of the image, is positioned at the interference filter I, FIG. 23, decentered in relation to the beam cross-section, so that it covers about 15% of the beam width.

FIGS. 24a–24d show a series of SPR-images of a sensor surface exposed to rinse solution in a flow cell, the sensor surface consisting of sixteen zones of various refractive index (optical thickness), zone size 0.5 mm×0.5 mm, each image at a specific angle of incidence increasing in the order from a) to d). The lower the position of the focused spot within the angle-detecting area of the CCD, the larger is the angle of incidence. The angle of incidence is 65.9° in FIG. 24a, 66.4° in FIG. 24b, 66.9° in FIG. 24c, and 67.4° in FIG. 24d.

Since a change in the angle for SPR of 0.1° here corresponds to a change in the refractive index of 0.001 within the zone's reactive layer, the shift in refractive index is 0.005 between FIGS. 24a and 24b, 24b and 24c, and 24c and 24d, respectively.

At SPR within a specific zone, detected as a minimum of light reflected in the zone, the corresponding angle of incidence is a measure of the refractive index (optical thickness) of the zone. The larger the angle of incidence at SPR is, the larger is the optical thickness (or refractive index at fixed thickness), which corresponds to a larger surface concentration of bound sample to a zone.

Figure 24A:
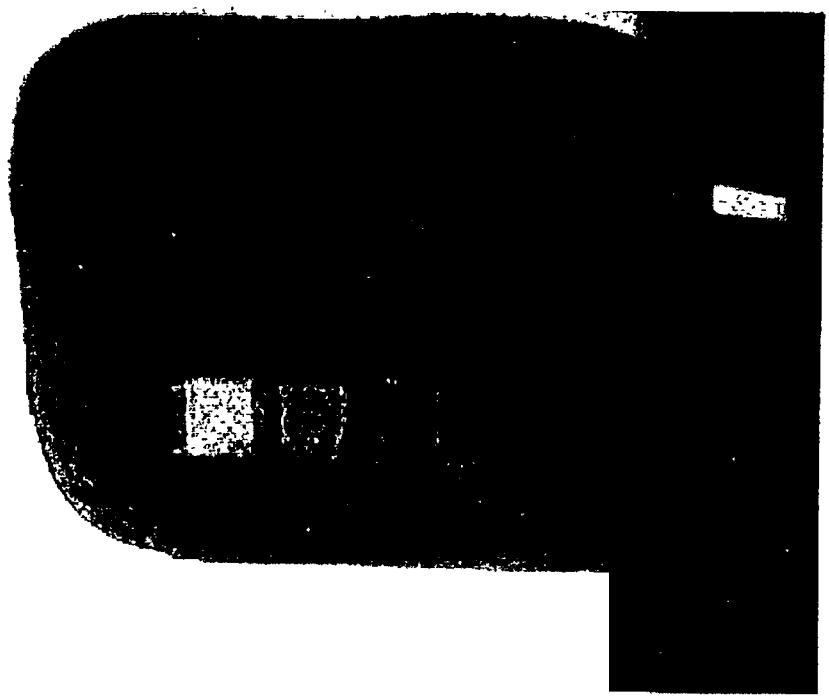
FIGS. 24a to 24d are SPR-images of a sensor surface.
Figure 24B:
Figure 24C:
Figure 24D:

In FIG. 24a the following zone-coordinates (row, column) show light extinction due to SPR: (1,1), (1,2), (1,3), while the higher angle of incidence in FIG. 24b causes SPR in the zones: (2,1), (2,2), (3,1), (3,2), revealing a higher surface concentration in the latter zones. In FIG. 24c, the zones of the sensor surface having yet higher surface concentration of sample are revealed in zones (4,2) and (4,3). In FIG. 24d, the zone of the sensor surface having the highest surface concentration of sample are revealed in zone (4,1).

As an example, the refractive index in zone (3,1) is 0.005 higher than the one for zone (1,1), while the refractive index in zone (4,2) is 0.005 higher than the one for zone (2,1), and the refractive index in zone (4,1) is 0.015 higher than the one for zone (1,1).

The above-described results demonstrate the function of the present invention, an optical apparatus for multi-zone quantitative analysis on a sensor surface by use of simultaneous measuring of zone-data and angle-data on the same photodetector matrix. It is then readily appreciated by a person skilled in the art, that a suitable evaluation computer program could provide a high-sensitive and fast determination of the angle for SPR for specific sensor zones by combining a first computer program for one-dimensional spot-position analysis with a second computer program for two-dimensional intensity-pattern analysis.

Furthermore, it is readily appreciated by a person skilled in the art, that the invention also provides for measurement of zone-data on a photodetector matrix and a simultaneous measurement of angle-data on a separate detector.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of determining interaction of at least one species with a plurality of individual zones of a sensing surface, which method comprises:
   contacting the sensing surface with a fluid sample containing at least one surface interacting species,
   irradiating the surface with light so that the light is internally or externally reflected at the surface,
   imaging reflected light on a first photo-detector, each individual sensing surface zone corresponding to a respective area of the detector,
   sequentially or continuously scanning the incident angle at the sensing surface and/or the wavelength of the light over an angular and/or wavelength range,
   measuring the intensities of light imaged on different areas of the detector, at at least a number of incident angles and/or wavelengths to create a series of images of the sensing surface,
   simultaneously measuring the momentary incident angle and/or wavelength of the scanned light on a second photo-detector to correlate each image to a specific incident angle and/or wavelength, and
   determining from the relationship between image intensity data and angular and/or wavelength data, interaction of the species with the individual sensing surface zones.

2. The method according to claim 1, wherein the incident angle and/or wavelength and the image area intensities of light are measured on a common detector.

3. The method according to claim 1, wherein the incident angle of the light is scanned.

4. The method according to claim 1, wherein the wavelength of the light is scanned.

5. The method according to claim 1, wherein the light is internally reflected from the surface.

6. The method according to claim 1, wherein the light is externally reflected from the surface.

7. The method according to claim 1, wherein the light is coupled to the surface via a prism.

8. The method according to claim 1, wherein the light is coupled to the surface via a grating.

9. The method according to claim 1, wherein the image forming is based on surface plasmon resonance.

10. The method according to claim 1, wherein the determined interaction is a chemical or biochemical binding interaction.

11. The method according to claim 1, wherein the determined interaction is a physical or biophysical interaction.

12. The method according to claim 1, wherein the fluid sample is contacted with the sensing surface in a flow cell.

13. The method according to claim 1, which comprises reading image intensity data into an image data memory and reading angular and/or wavelength data into an angular data memory and/or a wavelength data memory.

14. An analytical system, comprising:
    a sensor unit having a sensing surface with a number of individual zones,
    means for illuminating the sensing surface with a collimated beam of light,
    means for imaging reflected light from the illuminated sensing surface into an image plane,
    means for sequentially or continuously scanning the light incident at the sensing surface over a range of incident angles and/or wavelengths,
    means for synchronized optical detection of images in the image plane and incident angle and/or wavelength of light illuminating the sensing surface, and
    evaluation means for determining from the relationship between detected intensity of different parts of the images and incident light angle and/or wavelength, the optical thickness of each zone of the sensing surface.

15. The system according to claim 14, wherein the means for synchronized optical detection comprises integral photodetector means.

16. The system according to claim 14, wherein the means for scanning comprise beam deflecting means to produce an angle-scanned collimated illumination of the sensing surface, each sensing surface zone momentarily being illuminated by light rays of identical angle of incidence and wavelength.

17. The system according to claim 16, wherein the evaluation means comprise an evaluation unit for determining the angle, and/or the wavelength, for minimum reflectance of p-polarized light, and/or the relative reflectance and phase of the p- and s-polarized electric field components of the light for each of the individual zones of the sensing surface.

18. The system according to claim 16, wherein sensing surface supports reactants capable of binding interaction with species in a sample.

19. The system according to claim 14, wherein the system comprises a sample solution container in contact with the sensing surface to expose the sensing surface to sample solution.

20. The system according to claim 19, wherein the sample solution container is a flow cell.

21. The system according to claim 19, wherein the collimated light beam is p-polarized.

22. The system according to claim 14, wherein the system is based on total internal reflection versus angle and/or wavelength of incidence.

23. The system according to claim 22, wherein the system is based on surface plasmon resonance, Brewster angle, ellipsometry, critical angle, or frustrated total reflection waveguide resonance.

24. The system according to claim 14, wherein the system comprises computer means.

* * * * *